(12) United States Patent
Orol et al.

(10) Patent No.: US 11,609,159 B2
(45) Date of Patent: Mar. 21, 2023

(54) SYSTEMS, DEVICES, AND METHODS FOR AGRICULTURAL SAMPLE COLLECTION

(71) Applicant: The Trustees of the University of Pennsylvania, Philadelphia, PA (US)

(72) Inventors: Daniel Orol, Raleigh, NC (US); Lukas Vacek, Philadelphia, PA (US); Delaney Vanessa Kaufman, Rolling Hills Estates, CA (US); Jnaneshwar Das, Philadelphia, PA (US); R. Vijay Kumar, Wilmington, DE (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1181 days.

(21) Appl. No.: 15/974,243

(22) Filed: May 8, 2018

(65) Prior Publication Data
US 2018/0335372 A1    Nov. 22, 2018

Related U.S. Application Data

(60) Provisional application No. 62/503,170, filed on May 8, 2017.

(51) Int. Cl.
*G01N 1/08* (2006.01)
*B64C 39/02* (2023.01)
(Continued)

(52) U.S. Cl.
CPC .............. *G01N 1/08* (2013.01); *A01G 3/00* (2013.01); *B64C 39/024* (2013.01);
(Continued)

(58) Field of Classification Search
CPC .................. B64C 39/02; B64C 39/024; B64C 2201/024; B64C 2201/12; A01G 3/00;
(Continued)

(56) References Cited

U.S. PATENT DOCUMENTS

| 4,037,476 A * | 7/1977 | McCrabb ................. G01N 1/08 73/864.31 |
| 4,072,059 A * | 2/1978 | Hamilton ................. G01N 1/08 73/864.33 |

(Continued)

OTHER PUBLICATIONS

Rains et al., "Steps toward an Autonomous Field Scout and Sampling System," Agricultural and Biological Engineering (ASABE) International Conference, pp. 1-14 (2015).

(Continued)

*Primary Examiner* — Peter J Macchiarolo
*Assistant Examiner* — Mohammed E Keramet-Amircolai
(74) *Attorney, Agent, or Firm* — Jenkins, Wilson, Taylor & Hunt, P.A.

(57) ABSTRACT

The present subject matter relates to systems, devices, and methods for agricultural sample collection. In one aspect, a sample collection system includes an aerial robotic platform, an arm assembly coupled to the aerial robotic platform and comprising an arm that extends away from the aerial robotic platform, and a sample collector connected to a distal end of the arm, wherein the sample collector is configured to selectively remove one or more samples of agricultural material from a plant to be analyzed.

18 Claims, 12 Drawing Sheets

(51) Int. Cl.
*A01G 3/00* (2006.01)
*G01N 33/00* (2006.01)
*G01N 1/00* (2006.01)
*G01N 1/28* (2006.01)

(52) U.S. Cl.
CPC .... *G01N 33/0098* (2013.01); *B64C 2201/024* (2013.01); *B64C 2201/12* (2013.01); *G01N 2001/002* (2013.01); *G01N 2001/085* (2013.01); *G01N 2001/2833* (2013.01)

(58) Field of Classification Search
CPC .... G01N 33/00; G01N 1/08; G01N 2001/002; G01N 2001/085; G01N 33/0098
USPC ..................................................... 73/864.31
See application file for complete search history.

(56) References Cited

U.S. PATENT DOCUMENTS

| | | | | |
|---|---|---|---|---|
| RE30,901 E * | 4/1982 | Boxrud | ................. | G01N 1/08 172/22 |
| 4,526,045 A * | 7/1985 | Reekie | ................... | G01N 1/10 376/245 |
| 4,665,758 A * | 5/1987 | Schaarschmidt | ........ | G01N 1/10 73/863.32 |
| 5,309,774 A * | 5/1994 | Conche | ................... | G21F 7/06 73/863.32 |
| 5,435,399 A * | 7/1995 | Peterson | ................. | E02D 1/04 175/135 |
| 7,631,834 B1 * | 12/2009 | Johnson | ............... | B64C 39/024 244/17.11 |
| 8,346,391 B1 * | 1/2013 | Anhalt | ................... | B25J 9/163 700/248 |
| 8,666,552 B2 | 3/2014 | Zeelen | | |
| 9,447,448 B1 * | 9/2016 | Kozloski | ................ | B64D 1/22 |
| 10,766,617 B2 * | 9/2020 | Gwin | ...................... | B64D 1/02 |
| 2007/0200027 A1 * | 8/2007 | Johnson | ............... | B64C 39/024 244/3.1 |
| 2014/0336848 A1 * | 11/2014 | Saund | ................... | G06T 7/215 701/3 |
| 2016/0011592 A1 * | 1/2016 | Zhang | ................... | G05D 1/102 701/2 |
| 2016/0137304 A1 * | 5/2016 | Phan | .................... | B64C 39/024 244/17.23 |
| 2016/0169772 A1 * | 6/2016 | Olmedo | .................. | G01N 1/08 73/864.32 |
| 2016/0302351 A1 * | 10/2016 | Schildroth | ............ | B64C 39/024 |
| 2016/0364989 A1 * | 12/2016 | Speasl | ................ | G08G 5/0069 |
| 2017/0023937 A1 * | 1/2017 | Loianno | ............... | G05D 1/0088 |
| 2017/0096222 A1 * | 4/2017 | Spinelli | .................. | B64C 33/00 |
| 2017/0200530 A1 * | 7/2017 | Davis | ...................... | H02G 1/02 |
| 2017/0225784 A1 * | 8/2017 | Hayes | ................... | B63B 21/50 |
| 2017/0372137 A1 * | 12/2017 | Kumar | .................. | H04N 7/185 |
| 2018/0001476 A1 * | 1/2018 | Tan | ......................... | B61G 7/04 |
| 2018/0257774 A1 * | 9/2018 | Volpi | ..................... | B25J 13/02 |

OTHER PUBLICATIONS

Vacek et al., "sUAS for Deployment and Recovery of an Environmental Sensor Probe," 2017 International Conference on Unmanned Aircraft Systems (ICUAS), pp. 1-9 (Jul. 2017).
An Aerial Phytobiopsy System: Design, Evaluation, and Lessons Learned, submitted to International Conference on Robotics and Automation, 2016., submitted Sep. 15, 2016 Video of system in action (also submitted to ICRA 2017): https://www.youtube.com/watch? v=JmjJXrCwpbU.
USDA, "Multipurpose Robotic Sampling to Optimize Crop Production," Georgia Tech Applied Research Corporation, pp. 1-6 (2018).
Das, "UPENN/USDA Pest-trap Recovery," Video: https://www.youtube.com/watch?v=hhLLx9dVL4Y (Jan. 22, 2017).
Microsoft Research Project Premonition, "Project premonition aims to detect pathogens before they cause outbreaks," https://www.microsoft.com/en-us/research/project/project-premonition/, pp. 1-12 (Mar. 2, 2015).
MAVROS—MAVLink extendable communication node for ROS with proxy for Ground Control Station. http://wiki.ros.org/mavros, pp. 1-26 (Accessed: Mar. 3, 2018).
Das, "Autonomous insect-trap deployment, NSF student UAV challenge," https://www.youtube.com/watch?v=SM1uK50p-Q4 (Oct. 9, 2016).
Gealy et al., "Date: A Handheld Co-Robotic Device for Automated Tuning of Emitters to Enable Precision Irrigation," 2016 IEEE International Conference on Automation Science and Engineering (CASE), pp. 1-6 (Aug. 21-24, 2016).
Ahlin et al., "Autonomous Leaf Picking Using Deep Learning and Visual-Servoing," The 5th IFAC Conference on Sensing, Control, and Automation in Agriculture (AgriControl 2016), pp. 177-183 (Aug. 14-17, 2016).
Sarkar et al., "Towards autonomous phytopathology: Outcomes and challenges of citrus greening disease detection through close-range remote sensing," in IEEE International Conference on Robotics and Automation. IEEE, pp. 5143-5148 (May 16-21, 2016).
Das et al., "Devices, systems, and methods for automated monitoring enabling precision agriculture," in 2015 IEEE International Conference on Automation Science and Engineering (CASE), pp. 462-469 (Aug. 24-28, 2015).
Garimella et al., "Towards Model-predictive Control for Aerial Pick-and-Place," 2015 IEEE International Conference on Robotics and Automation (ICRA), pp. 4692-4697 (May 26-30, 2015).
Meier et al., "PX4: A node-based multithreaded open source robotics framework for deeply embedded platforms," in Robotics and Automation (ICRA), 2015 IEEE International Conference on, pp. 6235-6240 (May 26-30, 2015).
Ruggiero et al., "A multilayer control for multirotor UAVs equipped with a servo robot arm," 2015 IEEE International Conference on Robotics and Automation (ICRA), pp. 1-7 (May 26-30, 2015).
Ore et al., "Autonomous aerial water sampling," Journal of Field Robotics, vol. 32, No. 8, pp. 1095-1113 (2015).
Stecker, T., "Scientists hunt citrus killer as industry hangs in balance," E&E News, pp. 1-3 (Sep. 15, 2015).
"Florida Citrus Statistics 2011-2012," United States Department of Agriculture, National Agricultural Statistics Service, pp. 1-118 (Feb. 2013).
Huber et al., "First analysis and experiments in aerial manipulation using fully actuated redundant robot arm," in IEEE/RSJ International Conference on Intelligent Robots and Systems, pp. 3452-3457 (Nov. 3-7, 2013).
Sreenath et al., "Geometric Control and Differential Flatness of a Quadrotor UAV with a Cable-suspended Load," in 52nd IEEE Conference on Decision and Control, pp. 2269-2274 (Dec. 10-13, 2013).
Thomas et al., "Avian-Inspired Grasping for Quadrotor Micro UAVs," in IDETC/CIE, ASME, pp. 1-9 (2013).
Quigley et al., "ROS: an open-source Robot Operating System," in ICRA workshop on open source software, vol. 3, No. 3.2, pp. 1-6 (2009).
Mahvash et al., "Modeling the Forces of Cutting With Scissors," in IEEE Transactions on Biomedical Engineering, vol. 55, No. 3, pp. 848-856 (Mar. 2008).
Schmale et al., "Development and application of an autonomous unmanned aerial vehicle for precise aerobiological sampling above agricultural fields," Journal of Field Robotics, vol. 25, No. 3, pp. 133-147 (2008).
Luo et al., "Autonomous grasping of a space robot multisensory gripper," in Proceedings of the 2006 IEEE/RSJ International Conference on Intelligent Robots and Systems, pp. 1014-1019 (Oct. 9-15, 2006).

* cited by examiner

SYSTEMS, DEVICES, AND METHODS FOR AGRICULTURAL SAMPLE COLLECTION

PRIORITY CLAIM

The present application claims the benefit of U.S. Patent Application Ser. No. 62/503,170, filed May 8, 2017, the disclosure of which is incorporated herein by reference in its entirety.

GOVERNMENT INTEREST

The presently disclosed subject matter was made with U.S. Government support under Grant No. 2015-67021-23857 awarded by the U.S. Department of Agriculture, and National Science Foundation Grant No. CNS-1521617. Thus, the U.S. Government has certain rights in the presently disclosed subject matter.

TECHNICAL FIELD

The subject matter disclosed herein relates generally to systems and methods for early plant disease detection. More particularly, the subject matter disclosed herein relates to systems, devices, and methods for collection of agricultural samples such as leaf, pests, and soil.

BACKGROUND

Plant diseases severely impact crop growth and yield, with significant economic impact in the US from citrus greening disease alone. Current phytopathology methods utilize detection via specialized optics [1], as well as manual sample collection for ex situ analysis. For example, affected trees in a citrus grove may be spotted by workers walking or riding vehicles through the grove, with each grove being surveyed four or more times a year. The affected trees are visually identified due to their mottled appearance, and samples from the trees are then tested in laboratories to rule out other conditions. However, various diseases cannot be visually distinguished with certainty, even by experts, making visual methods often unsuitable for precise diagnosis. In addition, conventional ground-based sampling systems and human scouts often cannot see or access the tops of trees.

Furthermore, certain physical sampling tasks require long dwell-times to collect sufficient populations of the target specimens. For example, pest traps are conventionally deployed across farms and recovered manually after days or weeks for pest density estimation.

In both the cases of discrete plant sampling and longer-term environmental monitoring, although human experts can detect symptomatic trees, and if necessary, collect samples for ex-situ analysis, manual sample collection is not scalable for multiple reasons. First, many farms are simply too large, resulting in under-sampling. For example, watermelon plots can span up to 100 acres, with scouts having around 10-15 minutes to inspect them. Second, once a scout obtains a sample, she must transport it to a lab equipped with molecular or morphological analysis equipment for precise identification of the disease as well as its stage. Conventional sampling methods thus suffer from being labor-intensive, time-consuming, and often require researchers to traverse difficult terrain.

As a result, current phytopathology methods are considered imprecise if not inadequate for early plant disease detection.

SUMMARY

In accordance with this disclosure, systems, devices, and methods for agricultural sample collection are provided. In one aspect, a novel, low-cost aerial phytobiopsy system, for robust and reliable plant sample acquisition for ex-situ analysis is provided. Such a system may include an aerial robotic platform, an arm assembly coupled to the aerial robotic platform and comprising an arm that extends away from the aerial robotic platform, and a sample collector connected to a distal end of the arm, wherein the sample collector is configured to selectively remove one or more samples of agricultural material from a plant to be analyzed. Using such a system, plant samples may be collected with a low dwell-time (e.g., within seconds) to enable quick analysis.

In another aspect, the presently-disclosed subject matter provides a method for acquiring agricultural samples. The method may include positioning an aerial robotic platform in proximity to a plant to be analyzed, grasping a portion of the plant to be analyzed, selectively removing one or more samples of agricultural material from the plant to be analyzed, and transporting the one or more samples to a remote location for ex-situ analysis of the one or more samples.

In another aspect, the presently-disclosed subject matter provides an agricultural sample collection system comprising an environmental sensor probe comprising a first coupling member including a first engagement element and an aerial robotic platform comprising a second coupling member including a second engagement element configured to be selectively coupled to the first engagement element. The environmental sensor probe may comprise a sample collector, wherein the sample collector is configured to receive one or more environmental samples therein to be analyzed. In some embodiments, such a system may be deployed for persistent collection of air, soil, and pest samples with a high dwell-time (e.g., over the course of hours or days).

In yet another aspect, a method for acquiring agricultural samples comprises positioning an environmental sensor probe in an area in proximity to a plant to be analyzed, collecting one or more environmental samples from the area in proximity to the plant to be analyzed in a sample collector of the environmental sensor probe, coupling the environmental sensor probe to an aerial robotic platform, and transporting the one or more environmental samples to a remote location for ex-situ analysis of the one or more environmental samples.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which.

DETAILED DESCRIPTION

The present subject matter provides systems, devices, and methods for agricultural sample collection that mitigate the challenges of existing phytopathology methods. In one aspect, the present subject matter provides systems, devices, and methods that may involve the use of a lightweight mechanical system capable of grasping, severing, storing, and transporting test samples (e.g., sections of leaves) from a plant. Alternatively or in addition, the present systems, devices, and methods may be configured to deploy and/or collect a separate environmental sensor probe that is designed to collect test samples at or near a plant.

In some embodiments, such systems are implemented using an aerial robotic platform that enables acquisition of samples for in-situ or ex-situ analysis. In some embodiments, for example, this platform allows for a diseased plant section, once identified, to be removed (substantially undamaged) and transported to a lab for analysis. Aerial manipulation is a rapidly growing field, with systems designed for autonomous grasping [2], [3], perching [4], and object manipulation [5]. Aerial manipulator systems have used various form factors and configurations such as lightweight quadrotors, heavy-lift hexrotors, and helicopters [6]. A co-robotic design of grippers is discussed by Gealy et al [7]. Despite these developments in aerial manipulation generally, these principles have yet to be adapted for use in phytopathology. Specifically, no method currently exists to acquire physical samples of symptomatic plant leaves using an aerial platform (e.g., for detailed phytopathological studies).

Figure 1:
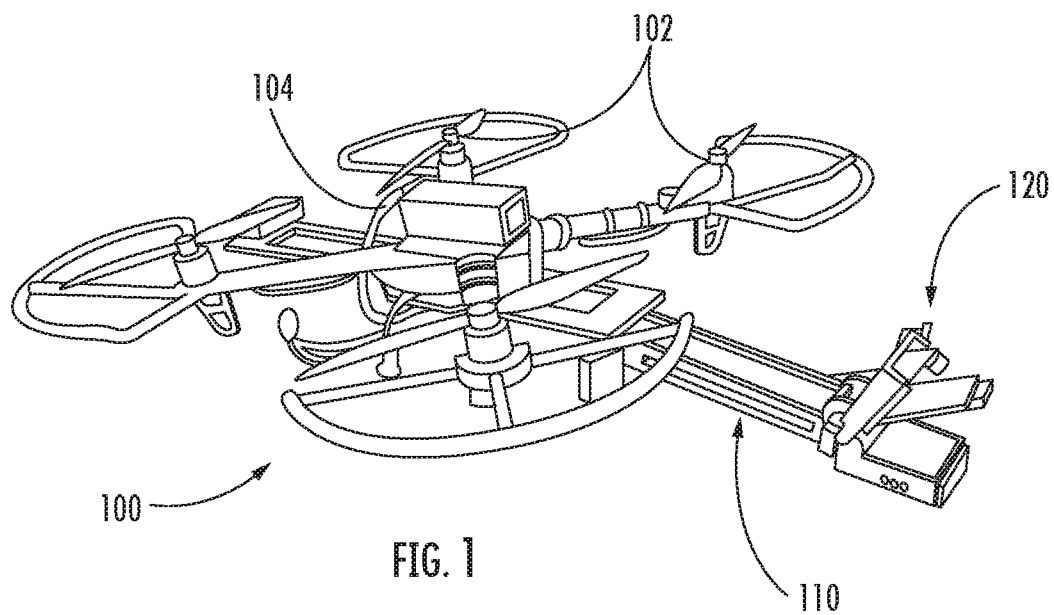
FIG. 1 is a perspective side view of a phytobiopsy UAV according to an embodiment of the presently disclosed subject matter.

Referring to the embodiment shown in FIG. 1, in some embodiments, the aerial robotic platform, generally designated 100, is an unmanned aerial vehicle (UAV) platform (e.g., a quadcopter) that is configured for reliably collecting symptomatic leaves from plants of interest. As used herein, the term unmanned aerial vehicle (UAV) is understood to include an aerial robotic platform that may be controlled remotely by a human or with onboard computers, and which may be capable of carrying payloads. In some common configurations, aerial robotic platform 100 may be a quadrotor vehicle as shown in FIG. 1, with four propellers 102 being arranged about a central power and control system 104, which may contain any of a variety of components that are configured to control the operation of aerial robotic platform 100, such as one or more transceivers, power supplies, power regulators, and/or motor drivers. UAVs are well-suited for precision agricultural tasks due to their small size, superior mobility, and hover capability, which allows them to perform close inspection (e.g., at distances less than 2 m) of problematic areas at a range of altitudes. In one example implementation selected for a balance of maneuverability and low-cost, aerial robotic platform 100 may be a DJI F450 airframe with motor-motor diameter of 45 cm, a Pixhawk flight controller, and a DJI E310 propulsion system. Power for aerial robotic platform 100 may be provided by a 4-cell 4000 mAh Multistar lithium polymer battery or the like.

As indicated above, aerial robotic platform 100 may be configured to grasp, sever, store, and transport test samples from a plant. To achieve this functionality, in some embodiments, an arm assembly, generally designated 110, may be coupled to aerial platform 100 and extend away from aerial platform 100, and a sample collector 120 may be connected to an end of arm assembly 110 (e.g., a distal end of the arm), such as is shown in FIG. 1. The example configurations discussed herein each refer to implementation on an aerial robotic platform 100 (e.g., a UAV), but those having ordinary skill in the art will recognize that the principles discussed herein regarding a sample collector 120 mounted to an arm assembly 110 may be adapted for use in other configurations (e.g., by ground robots, by a human for handheld use).

Figure 2A:
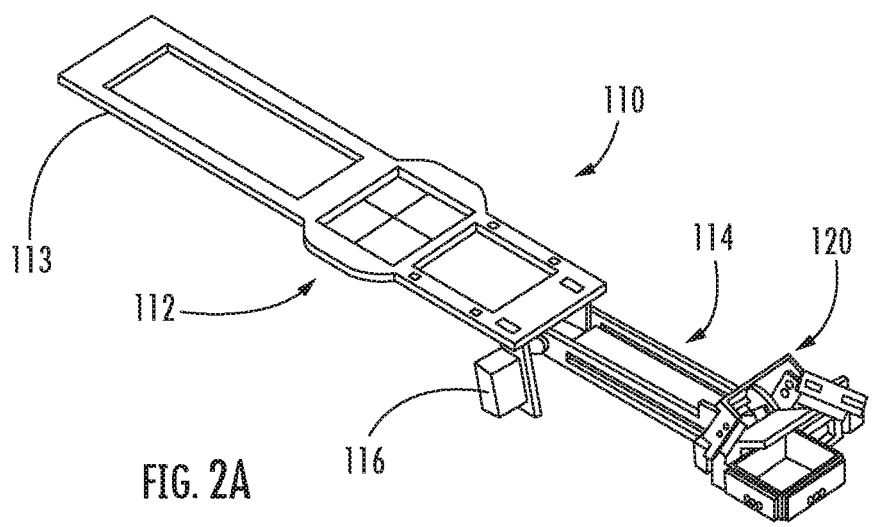
FIG. 2A is a perspective side view of an arm assembly for a phytobiopsy UAV in an extended position according to an embodiment of the presently disclosed subject matter.
Figure 2B:
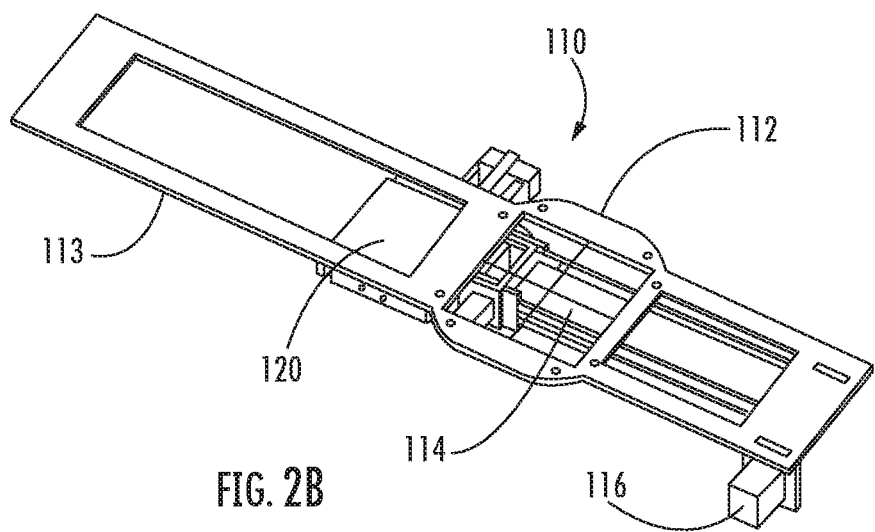
FIG. 2B is a perspective side view of an arm assembly for a phytobiopsy UAV in a retracted position according to an embodiment of the presently disclosed subject matter.

Referring to one embodiment shown in FIGS. 2A and 2B, arm assembly 110 may comprise a base 112 that is configured to be coupled to aerial robotic platform 100 (e.g., to a bottom surface of the UAV platform) and an arm 114 that is coupled to base 112 and extends away from aerial robotic platform 100. In some embodiments, arm 114 is configured to be selectively extendible such that it can extend away from aerial robotic platform 100 when needed but can be retracted as needed. As illustrated in FIG. 2A, such extension may be effected by a servo motor 116 (e.g., a JR DS8411 servo with 11.2 kg-cm of stall torque) that is coupled to the extendible arm and that is operable to selectively extend or retract the arm with respect to the base. The operation of arm 114 may be powered by a common power source that also supplies power to aerial robotic platform 100 (e.g., within housing 104), or it may receive power from a separate power source.

In this way, the design of arm 114 may be a simple, one-joint design. Alternatively, in some embodiments, arm 114 may be fixedly connected to base 112 such that it extends a fixed length away from aerial robotic platform 100. In any configuration, in some embodiments, arm 114 may be configured to provide an extra degree of freedom, wherein the flight system of aerial robotic platform 100 controls the height of arm 114 and it's yaw angle relative to the plant to be studied, but arm 114 can itself be further configured to roll through a range of angles (e.g., about 180 degrees, with the limits parallel to the base of aerial robotic platform 100). This additional range of motion increases the grasping ability, for example, to acquire samples from canopies very close to ground. The weight added to aerial robotic platform 100 by arm assembly 110 may be reduced by making arm assembly 110 out of a thin but stiff material (e.g., carbon fiber).

In any configuration, base 112 may include a counterweight portion 113 that extends in a direction substantially opposing arm 114 and that is sized and/or otherwise configured to at least partially offset the weight of arm 114 and thus diminish the effect of any imbalance in the operation of aerial robotic platform 100 that is created by the extension of arm assembly 110 in one direction away from aerial robotic platform 100. In some embodiments, for example, a battery that powers the operation of arm 114 and/or sample collector 120 may serve as counterweight 113 to keep the system stable without using a specialized controller.

Alternatively or in addition, an adaptive or sliding mode controller may be configured to account for the moving offset mass. Even in configurations where no counterbalancing is provided, and even when accounting for worst-case moment calculations (i.e., point masses with weight safety margins assumed), it can be shown that the configurations discussed herein for an aerial robotic platform 100, with arm 114 fully extended, would be able to hover without either set of motors of aerial robotic platform 100 exceeding 86% of their max thrust. In indoor applications, this is enough thrust to avoid saturating the motors. Furthermore, experimental tests with sample collector 120 attached show that the aerial robotic platform 100 can take off at around 50% thrust, thus satisfying the 2:1 thrust-to-weight ratio for hover typically desired for UAVs.

Referring again to the configuration discussed above in which arm 114 is selectively extendible to obtain a sample, arm 114 may be moved to a storage position. As illustrated in FIG. 2B, for example, in some embodiments, arm 114 can be rotated to a storage position in which sample collector 120 is stored beneath aerial robotic platform 100 when in flight mode so that the system's center of mass is substantially in the middle of the robot. In sample acquisition mode, arm 114 is extendible (e.g., as shown in FIG. 2A), at which point a secondary controller may be used to take hold and stabilize the off-center mass for the short period of time required to acquire a sample.

For use with this configuration, sample collector 120 that is connected to an end of arm assembly 110 enables a detailed phytopathology analysis. In some embodiments, for example, sample collector 120 may include an on-board spectral analysis device that is configured to non-destructively analyze the plant health.

Figure 3A:
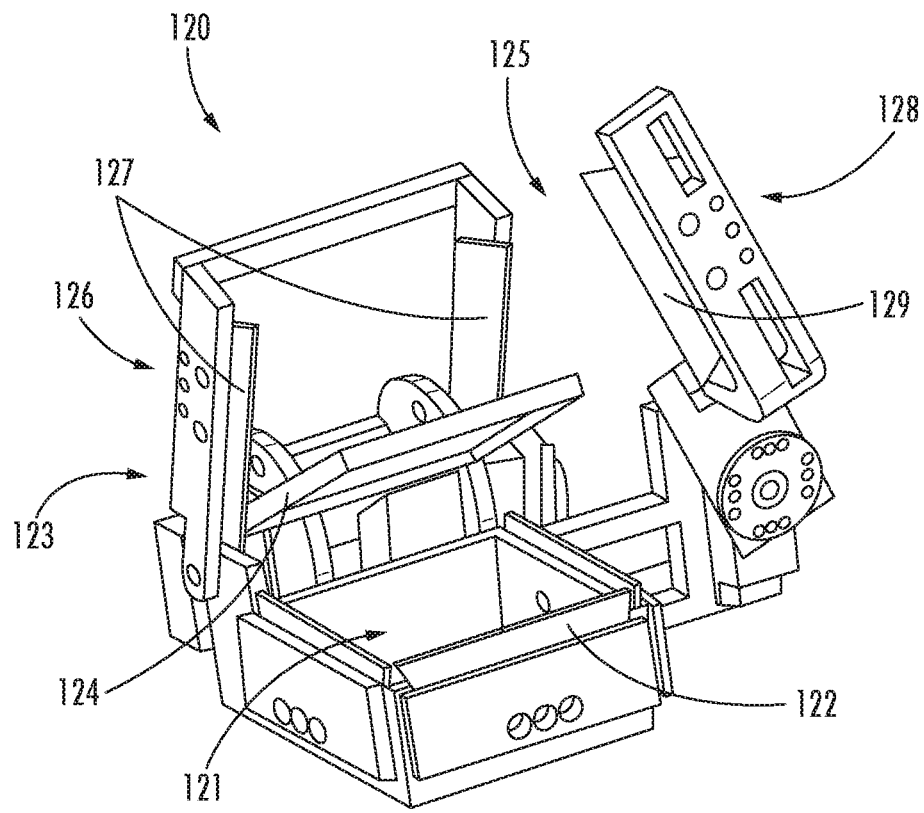
FIGS. 3A and 3B are perspective side views of a sample collector for a phytobiopsy UAV in two operating states according to an embodiment of the presently disclosed subject matter.
Figure 3B:
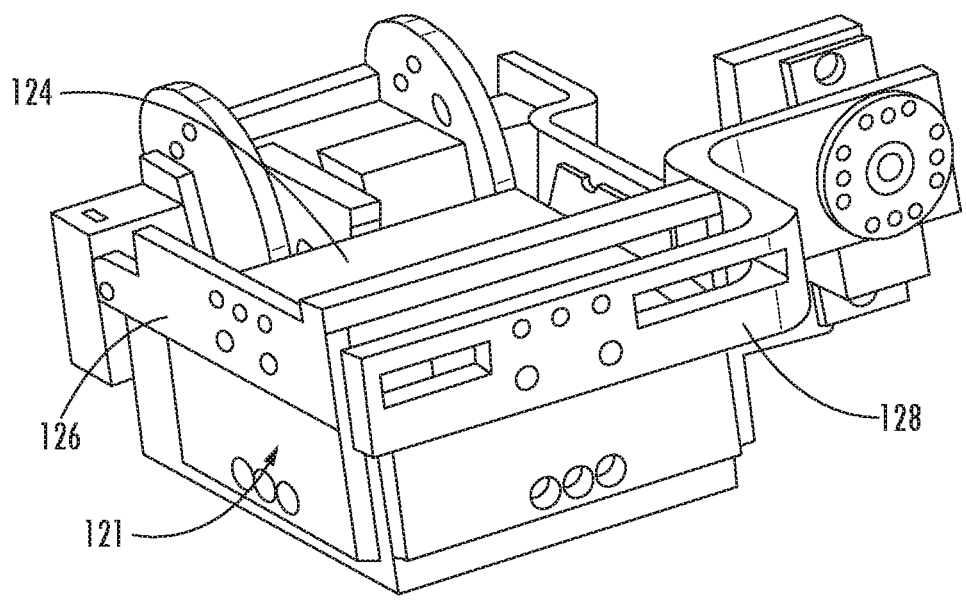

Alternatively or in addition, in some embodiments, sample collector 120 is configured to selectively remove a sample 150 of agricultural material (e.g., a portion of a leaf, stem, petiole) and transport it to a remote location for ex-situ analysis. In some embodiments, for example, sample collector 120 may be configured to grasp the plant to be analyzed, sever sample 150 from the plant (either concurrently with the grasping or by a separate action), and store it securely for transport. In particular, referring to the configuration illustrated in FIGS. 3A and 3B, sample collector 120 may include a receptacle 121 that is sized and shaped to receive the plant sample 150 (e.g., clumps of leaves, small flowers, or even pieces of stem) once it has been removed. In the illustrated embodiment, receptacle 121 is a substantially rectangular prism having side lengths that are designed such that receptacle 121 is large enough to receive a sample of a size that is sufficient to conduct a thorough analysis (e.g., having side lengths of approximately 5.3 cm). That being said, the size and weight of receptacle 121 may be limited to avoid significantly affecting the dynamics of a given aerial robotic platform 100 as discussed above. If a larger receptacle 121 is desired to accommodate larger samples, however, the specifications of aerial robotic platform 100 may be selected to allow for such an increase in payload size. (e.g., implemented as a hexrotor rather than a quadrotor)

In some embodiments, receptacle 121 may be particularly configured to prevent contamination (e.g., can be closed/sealed to prevent unwanted materials from entering the receptacle) to help maintain the integrity of sample 150 during transit. Furthermore, in some embodiments, receptacle 121 may be configured to collect multiple samples 150 on one flight without cross-contamination.

Sample collector 120 may further include a gripper assembly 123 that is configured to securely hold the material to be sampled. The design of the illustrated gripper assembly 123 is similar in concept to a mouth, with an upper peripheral edge 122 of receptacle 121 forming a first gripping element and a gripper tongue 124 that is movable (e.g., pivotable) with respect to receptacle 121 forming a second gripping element. In some embodiments, lightweight and inexpensive servos (e.g., a Tower Pro SG90 servo with 1.8 kg-cm of stall torque) may be used for actuating the movement of gripper tongue 124. The operation of these actuators may be powered by a common power source that is used to supply power to aerial robotic platform 100 in general (e.g., as part of power and control system 104), by a separate power source that drives the operation of arm assembly 110 (e.g., and forms part of counterweight 113), or it may receive power from a dedicated power source (e.g., a 3-cell, 1300 mAh Turnigy battery attached to a Drok 5 amp regulator set to 5 volts). Those having ordinary skill in the art will recognize, however, that any of a variety of other configurations for gripper assembly 123 may be used to hold the plant material in position. In some embodiments, for example, gripper assembly 123 may use a finger-like end effector, which is common for grasping tasks.

Figure 4:
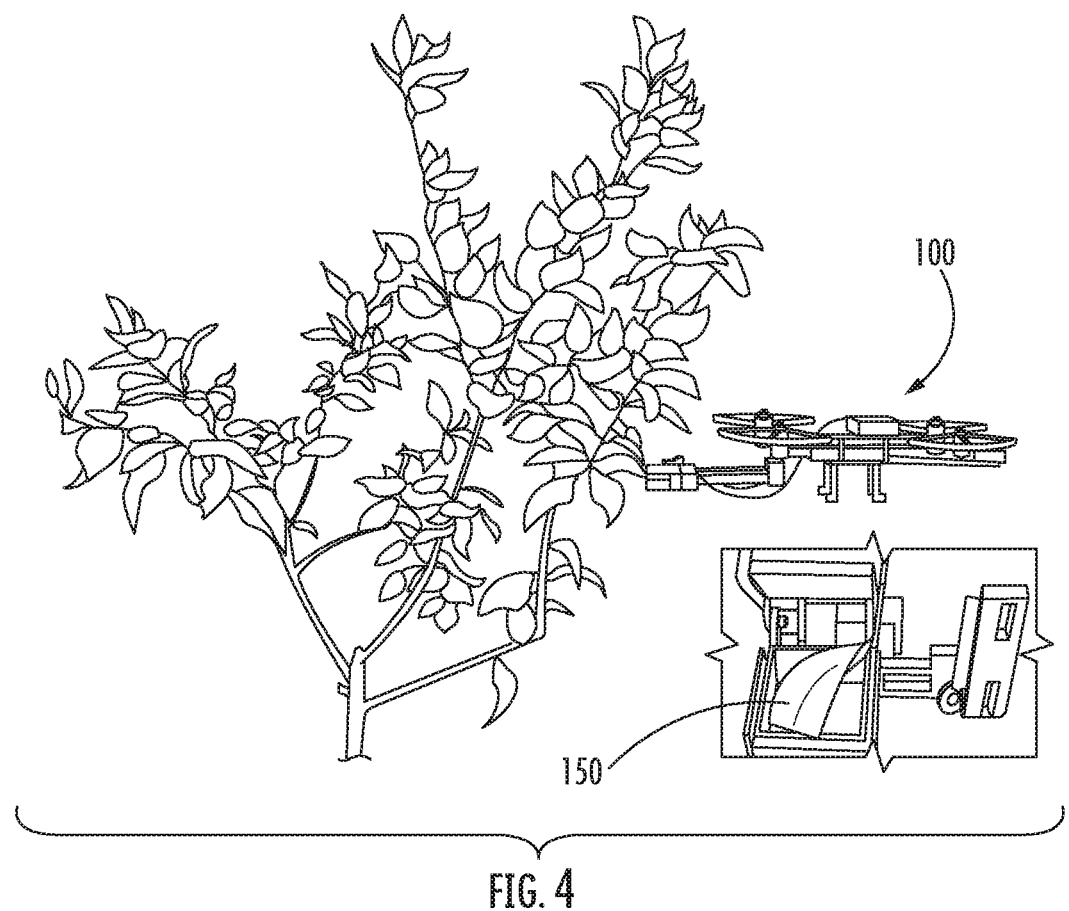
FIG. 4 is a side view of a phytobiopsy UAV during a flight trial according to an embodiment of the presently disclosed subject matter.

In any configuration, the ability to grip the plant material can be advantageous for both analyzing it in-situ or removing a portion for ex-situ analysis at another location since aerial manipulation can be difficult due to relative movement between aerial robotic platform 100 and the plant to be studied (e.g., due to wind, UAV rotor downwash). If not addressed, such relative movement could result in unpredictable and/or inconsistent sample retrieval. By gripping the plant material, however, aerial robotic platform 100 can be at least somewhat stabilized so that the sample may be collected more consistently. (See, e.g., FIG. 4)

Regarding the collection of the sample, sample collector 120 further includes a cutting assembly 125 that is configured to selectively remove a portion of the plant material to be sampled. Referring again to the configuration illustrated in FIGS. 3A and 3B, cutting assembly 125 may include a first cutter arm 126 that is movable with respect to gripper assembly 123 and that includes one or more first blades 127 attached thereto and a second cutter arm 128 that is likewise movable with respect to gripper assembly 123 and that includes one or more second blades 129. In this arrangement, cutting assembly 125 is positioned about receptacle 121, with first blades 127 and second blades 129 being aligned with three outward facing sides of receptacle 121. In the configuration illustrated in FIGS. 3A and 3B, for example, two first blades 127 are configured to be substantially aligned with sides of receptacle 121 when actuated, and a single second blade 129 is configured to be substantially aligned with a front of receptacle 121 when actuated. This arrangement ensures that the plant material to be sampled (e.g., a leaf or petiole) is severed with consistency across many sample angles.

In some embodiments, each of the blades is a stock box cutter blade (e.g., about 5.3 cm long). Although such blades, unlike scissors, are tapered on both sides, they provide some advantages in their low cost, easy maintenance, and successful performance. As with the actuation of gripper tongue 124, operation of cutting assembly 125 may be performed using lightweight and inexpensive servos (e.g., the cutter arms may be actuated with a pair of Futaba S3102 servos with 3.7 kg-cm of stall torque), although the servos used for cutting assembly 125 may be slightly heavier than servos coupled with gear ratios in order to improve the reliability and avoid the issue of gear backlash. Additionally, using two servos instead of one heavier servo that sequentially actuates both sets of blades can result in some weight savings. The torque for the blades was partially dictated by related research by Mahvash et al. on scissor cutting force [10]. They showed that scissors could cut paper with 2.5 N of force. The weakest part of the present cutting mechanism can nominally apply 3.5 N of force. This force number was validated by confirming that the present system can cut through paper with the side blades, and all three sets of blades have shown an ability to reliably and consistently cut through target leaves. As a result, the use of increased strength motors is not necessary and would add weight.

Although one configuration for cutting assembly 125 is shown and described above, those having ordinary skill in the art will recognize that any of a variety of other cutting elements may be used to selectively remove sample 150. For example, such alternative configurations may involve the use of high-wattage laser cutting elements rather than mechanical blade elements. The use of these or other non-contact cutting elements can be advantageous to carry out multiple cuts without being decontaminated between sample collections. In any configuration, however, cutting assembly 125 may be designed to quickly and substantially non-destructively remove sample 150 for ex-situ analysis.

Figure 5A:
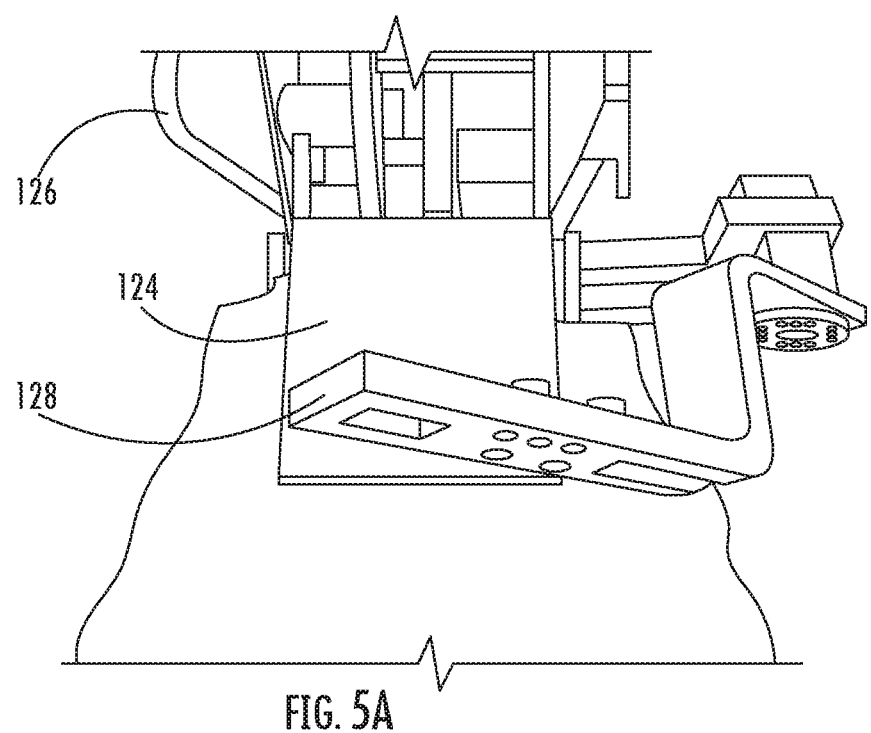
FIGS. 5A and 5B are top perspective views showing the operation of a sample collector for a phytobiopsy UAV according to an embodiment of the presently disclosed subject matter.
Figure 5B:
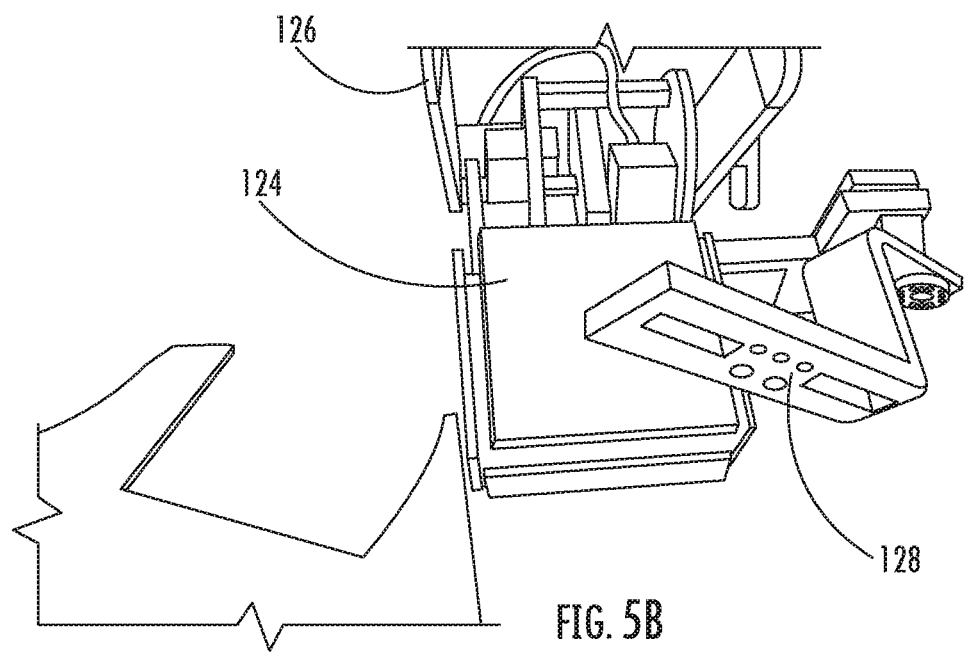

Referring to FIGS. 5A and 5B, the plant material to be sampled may be positioned between gripper tongue 124 and receptacle 121, and gripper tongue 124 may be moved to a closed position such that the plant material is clamped between the two elements. (See, e.g., FIG. 5A) With the plant material secured in this way, cutting assembly 125 may be actuated to sever a sample from the plant. (See, e.g., FIG. 5B) In such a configuration in which gripper tongue 124 may be actuated separately from cutting assembly 125, the grasping and cutting actions may be performed separately, which allows the system to attempt multiple cuts without releasing sample 150, which may help to ensure consistent results. Further, in addition to securing sample 150, gripper assembly 123 may be configured to create tension at the cutting interface. Since plant material is often relatively flexible, the creation of tension may help to prevent bending upon contact with cutting assembly 125, improving the system's performance with regards to many kinds of plant material (e.g., leaves and petioles). Further in this regard, sample collector 120 may be designed such that minimal space is provided on either side of the blades to help keep the plant material straight, improving the cutting ability of the sample collector.

To maximize performance, separate cutting actions may be performed by first blades 127 (i.e., the side blades) and second blades 129 (i.e., the front blade). In combination with a defined spacing between blades (e.g., about 0.127 mm of separation between blades, which lies within 3-D printing tolerance), this independent actuation allows for consistent cuts of the plant material.

In some embodiments, such as those illustrated, once the sample is severed from the plant, the sample may be stored in receptacle 121 to prevent contamination during transport. In the arrangement illustrated in the figures, for example, gripper tongue 124 may remain in a closed/clamping position to serve as a lid for receptacle 121, preventing non-target pathogens from contaminating sample 150. By combining storage and grasping mechanisms, such a configuration maintains mechanical simplicity while enhancing reliability. Alternatively or in addition, a separate lid element may be provided to close and/or seal the opening of receptacle 121 and thereby secure the plant sample 150 within receptacle 121. Further in this regard, multiple lid elements can be provided (e.g., all hinged along a common end like a book) to allow multiple independent samples to be stored separately within receptacle 121.

Figure 6:
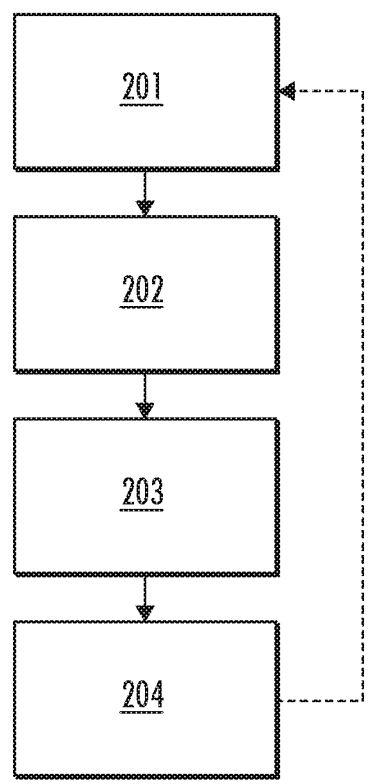
FIG. 6 is a flow chart illustrating a method for operating a phytobiopsy UAV according to an embodiment of the presently disclosed subject matter.

Although one particular form for sample collector 120 is shown and described herein, those having ordinary skill in the art will recognize that the principles discussed in the present disclosure may be implemented in any of a variety of other forms that are able to grasp, sever, store, and transport samples 150 from a plant. In any configuration, aerial robotic platform 100 discussed above is operable to consistently and repeatedly travel to a plant exhibiting signs of potential disease, grasp a portion of the plant (e.g., a leaf), cut sample 150 of the plant, store sample 150 in a closed receptacle, and transport sample 150 to a lab or other location for ex-situ analysis. Steps in such a repeatable process are shown, for example, in FIG. 6, in which a transport step 201 involves traveling to a desired plant, a grasping step 202 involves isolating the plant material to be excised, a cutting step 203 involves removing the plant material, and a storage step 204 involves securing the plant material for transport to a lab or other location for ex-situ analysis. In some embodiments, sample collector 120 can then be decontaminated as necessary, and aerial robotic platform 100 may be redeployed to collect additional samples from the same plant or from different plants.

As discussed above, the overall design of sample collector 120 may be configured to minimize and/or mitigate any relative movement of aerial robotic platform 100 with respect to the plant from which sample 150 is to be obtained. In particular, for example, the arrangement of arm assembly 110 and/or sample collector 120 with respect to aerial robotic platform 100 may be configured to account for downwash from aerial robotic platform 100. One way to address these effects is through precise positioning of the end-effector (e.g., sample collector 120) with respect to propellers 102 of aerial robotic platform 100. A set of experiments was conducted to qualitatively characterize the downwash in order to determine the placement of gripper assembly 123. In one test configuration, aerial robotic platform 100 was affixed using a rigid rod about two meters above the ground. The throttle was set to 20, 30, 35, and 40 percent while a branch was manually moved around beneath the robot. Observations were made for hover, roll, and pitch flight configurations, all of which change the relative thrusts of the motors. Propellers 102 generated wind caused significant changes to the leaf positions directly underneath aerial robotic platform 100, even in the center where there is no propeller. Different arrangements were also tested to see if placing objects in between propellers 102 and the plant helped. Three feasible options for end-effector placement were identified—a cable-winch system to extend arm assembly 110 beneath aerial robotic platform 100, a windscreen suspended below aerial robotic platform 100, or a configuration in which arm assembly 110 is extended out horizontally.

The cable-winch system is light and versatile, but in some configurations may involve considerable mechanical complexity for repeatable motions. More importantly, prior work has identified some controls challenges associated with such a system [8]. For the second option, a well-designed windshield would be centered and not affect controller performance, but precise aerodynamic shaping would be necessary in order to deflect the air around the plant, while not altering the thrust strength or motor efficiency. As opposed to the above two choices, the configuration of arm assembly 110 discussed above creates an off-center mass, but it is mechanically simple and controllable [9].

To control the operation of arm assembly 110 and gripper assembly 123, an independent control system may be provided with aerial robotic platform 100. In some embodiments, for example, a DX7 transmitter may be paired with a Spektrum AR8000 receiver to control the servos on arm assembly 114 and gripper assembly 123. The wires for the servos may be shielded (e.g., with aluminum foil) to avoid interference between gripper assembly 123 and the flight system. Aerial robotic platform 100 itself uses a Pixhawk flight controller running the open-source PX4 flight stack [11]. Flight status (e.g., battery voltage, flight mode) may be monitored, for example, using QGround-Control graphical user interface.

A controller within power and control system 104 may be configured to receive one or more inputs to determine an optimal approach trajectory in the presence of perturbations from wind as well as noise in state estimates. Such a controller may also be configured to compensate for the change of the center of mass when arm 114 is moved to an extended position.

In some embodiments, the present systems may be configured for autonomous flight, detection, manipulation, and verification. In this regard, gripper assembly 123 may be equipped with a camera (e.g., a 752×480 global-shutter RGB camera) that is configured to provide visual feedback for the cutting action. Additionally, such a visual input may be able to visually identify symptomatic leaves. For example, in some embodiments, the present systems, devices, and methods may be incorporated in heterogeneous robot teams that can autonomously search for crop diseases using vision algorithms and machine learning, and then collect samples of the diseased plant and transport it to a nearby lab for analysis.

Regardless of the particular configuration of the aerial robotic platform, in some embodiments, the cost of such as system may be under $700, and the total takeoff weight is 1.9 Kg.

Experimental Evaluation

Two sets of experiments were carried out: one with gripper assembly 123 detached to quantify the range of grasping and cutting actions as well as to qualitatively describe the types of leaves and stems that can be severed, and manual indoor flights to evaluate the success rate of leaf sample acquisition from a citrus tree. Citrus trees were chosen because of their relevance to early disease detection, but we attached other types of leaves from cutting trials on some flights to directly compare our two sets of experiments. In addition, however, leaves from citrus, rose, and watermelon plants are discussed herein as representative types of leaves that cover the spectrum of leaf characteristics. As discussed herein, the present systems, devices, and methods may be used to grasp both small leaves and sections of large leaves.

Figure 7:
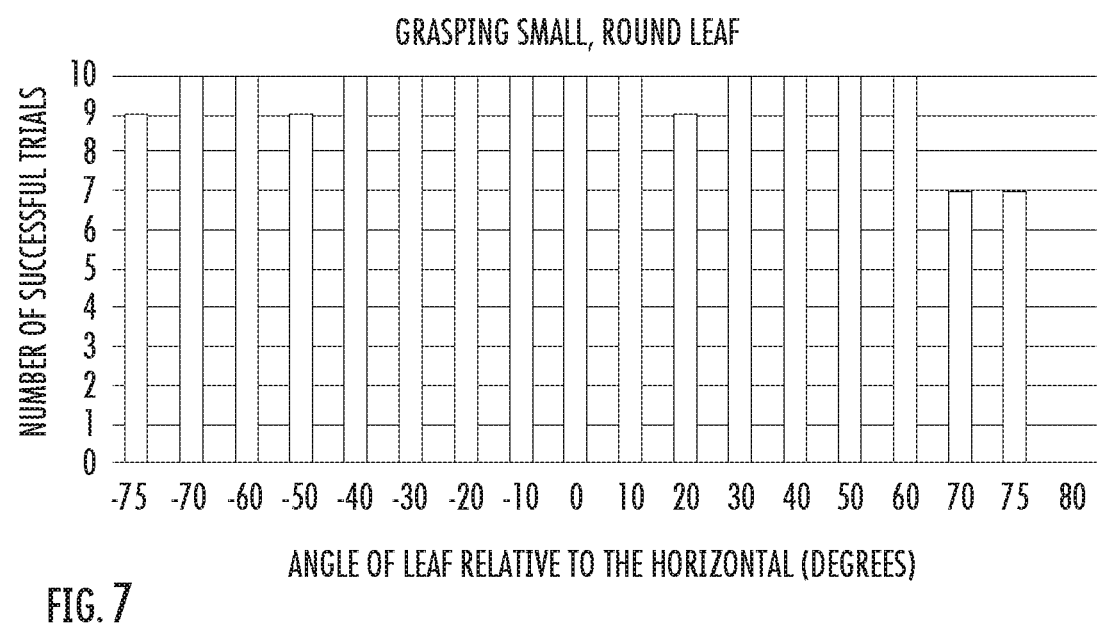
FIG. 7 is a chart illustrating the ability of a phytobiopsy UAV according to an embodiment of the presently disclosed subject matter to grasp small, round leaves over 10 trials.

In order to quantify how well the present systems can grasp leaves, tests were performed that compared the angle of a leaf to the number of successful grasping trials, some results of which are shown in FIG. 7. At each angle, the height of gripper assembly 123 was also adjusted to ensure that gripper assembly 123 could physically grasp the leaf before the 10 trials began. This test provided two key insights. First, the present system has very sharp cutoffs; if a leaf can be grasped once, it can be grasped reliably. Every set of trials with small leaves had either 0 successes, or at least 7 successes. This experiment demonstrated that with a properly calculated approach trajectory, gripper assembly 123 will succeed with high probability.

Second, the shape of the leaf doesn't matter significantly. Two differently-shaped but similarly sized kinds of leaves were tested; one was long and pointed, the other was short and round. The round leaf was also more rigid than the pointed leaf, but this did not impact the performance of the gripper assembly. The present systems are able to grasp both types of leaves over a large range of angles (e.g., from about 75 degrees below the horizontal to about 75 degrees above the horizontal). It is noted, however, that the lower ranges were limited by the experimental setup (i.e., the measuring apparatus interfered with larger negative angles), and thus it is contemplated that the systems may be able to grasp leaves at angles that exceed 75 degrees below the horizontal. Gripper assembly 123 reaching the experimental lower limit without running into any issues may be accounted for because the leaf could sit inside the receptacle rather than extend into the space between the receptacle and the gripper tongue.

Next, an investigation was conducted to see if large leaves could be grasped over the same angular range as small leaves. Such tests demonstrated that a large leaf could likewise be grasped over a large range of angles (e.g., ranging from about −75 to about 60 degrees relative to the horizontal). This range is less than the range measured for small leaves because of simple geometry: the stems of the large and the small leaves are held at the same angle, but the tip of the large leaf is further away from its stem, so the edge of that leaf sticks up past the reliable grasping zone. Experimental verification that the present systems, devices, and methods work similarly on many different shapes of leaves demonstrates the reliability and robustness of such systems.

Figure 8:
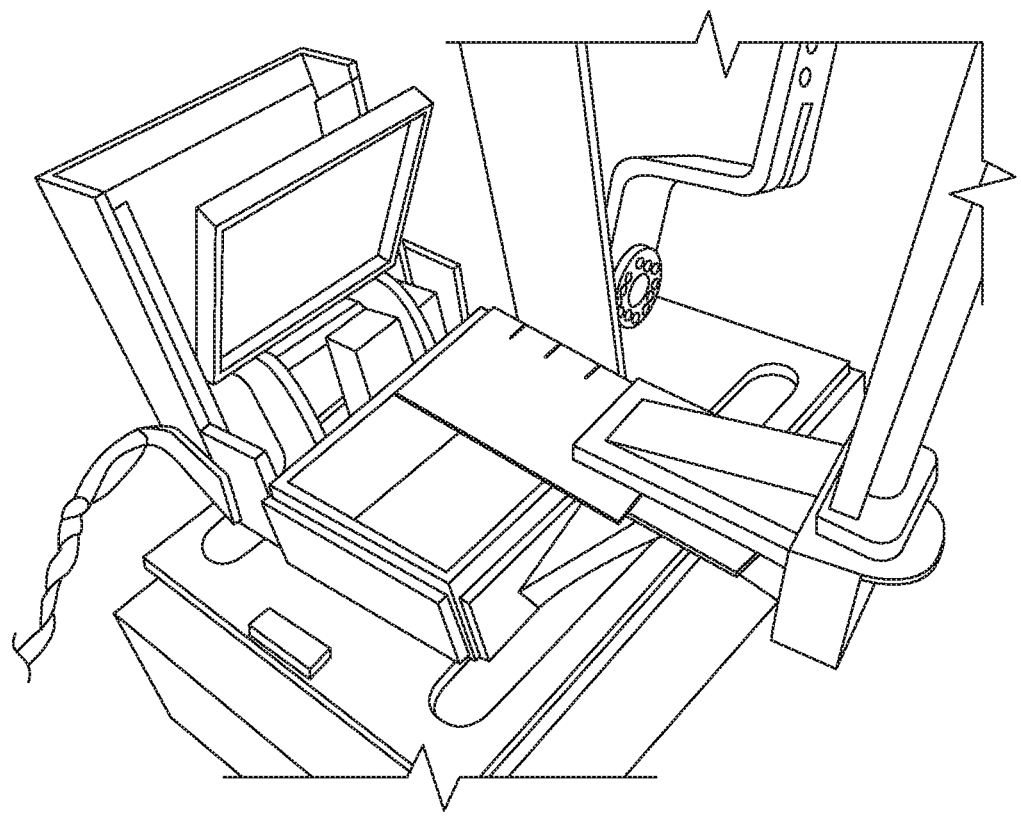
FIG. 8 is a top perspective view of a test configuration for a depth test for a phytobiopsy UAV according to an embodiment of the presently disclosed subject matter.

Leaves on trees will not have a specific angle of growth; they will show distributions of angle values. A second experiment addressed feasibility of use in real-world settings by studying the relation between leaf angle, depth, and height in successful sample acquisition. To avoid the bias of a particular type of leaf and maintain precise measurements, a piece of printer paper marked in half centimeter increments was used for this test (See, e.g., FIG. 8). For each angle, a new piece of paper was marked and clamped so that four centimeters were exposed. Measuring from the top of the storage receptacle, the height was varied by half centimeter increments from one centimeter until the paper could not be grasped. For each height, the paper was placed one, two, and three centimeters into the grasping mechanism. The angle varied from 0 to 50 degrees in 10 degree increments.

Figure 9:
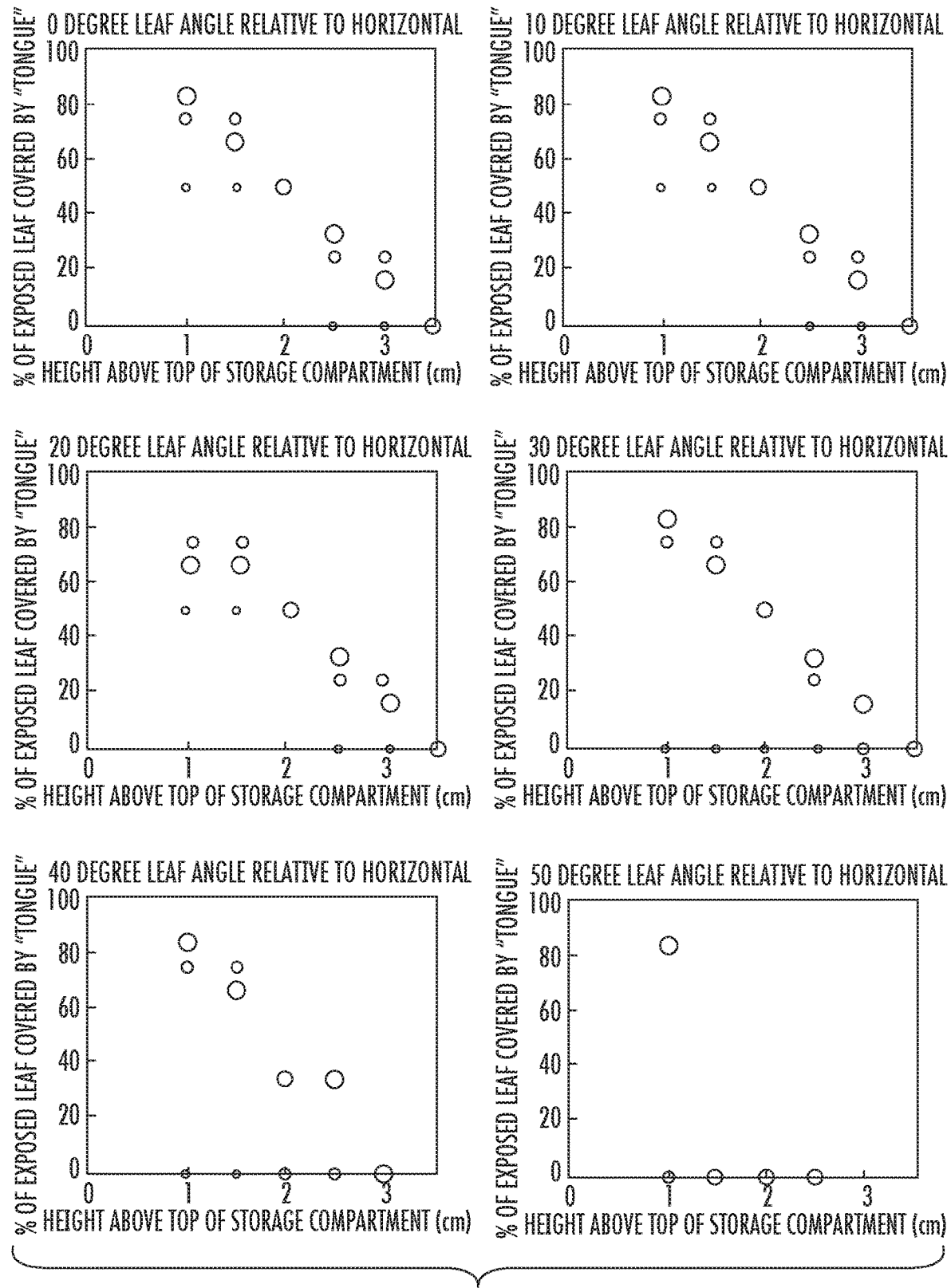
FIG. 9 is a chart illustrating results of a depth test with a paper leaf sample (for repeatability) for a phytobiopsy UAV according to an embodiment of the presently disclosed subject matter.
Figure 10:
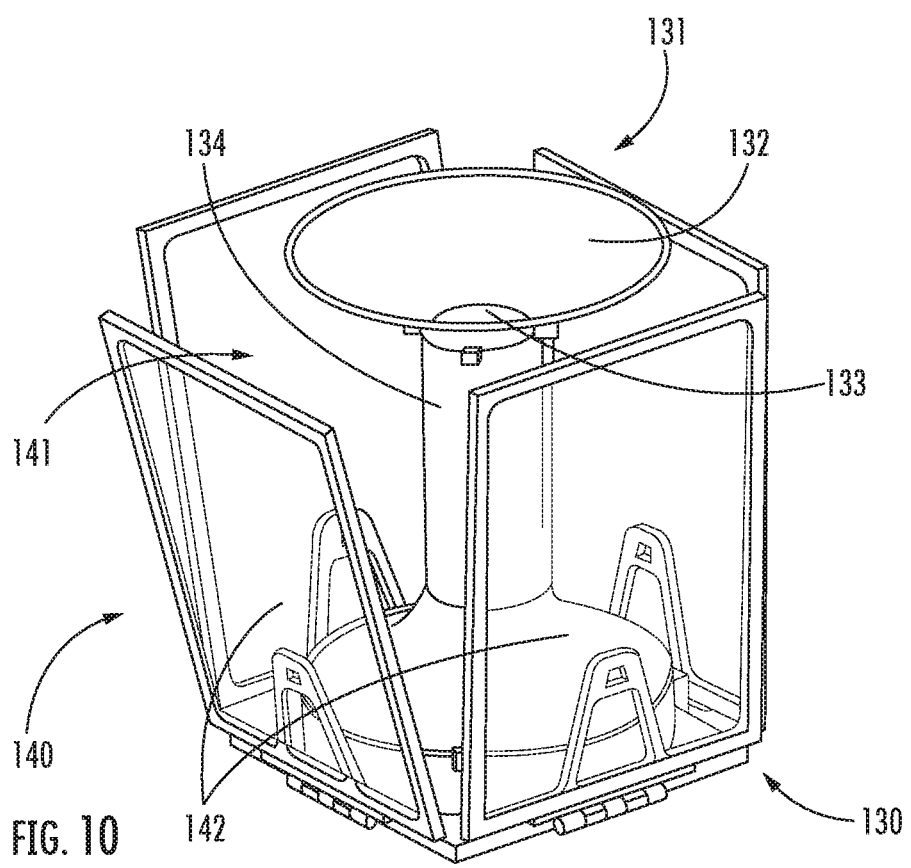
FIG. 10 is a perspective side view of an environmental probe configured to be deployed by a UAV according to an embodiment of the presently disclosed subject matter.

At each point, the largest covered increment was recorded. For example, if a paper was grasped so that the 1.5 cm mark was covered but the 2 cm mark was visible, a measurement of 1.5 cm was recorded as the covered measurement. Note that if the edge of the grasping mechanism was on a mark, that mark was considered to be covered. Not surprisingly, the ability of the present systems to grasp leaves decreased when less of the leaf was in range of the grasping mechanism, both horizontally and vertically. The mock leaves used for this test were similar in size to the small leaves that were used for the angle tests discussed above. The results are summarized in FIG. 9, with each graph showing a different angle, and each color showing a different depth into the gripper. In FIG. 10, the y-axis is normalized based on the depth of emulated leaf exposure, and the linear trend shows that the ability to grasp leaf samples drops off as it moves farther away from the storage box along the gripper assembly's vertical axis.

The experimental results demonstrate that the system is able to grasp leaves that enter gripper assembly 123 at a large range of angles, heights, and depths, highlighting feasibility for real-world use. Additionally, due to environmental or other perturbations when approaching a leaf, one cannot guarantee that aerial robotic platform 100 will remain perfectly in line with the leaf. However, the tests conducted demonstrate that even small leaves can be grasped as long as 1-2 cm of the leaf enters the system. Large leaves can enter further into gripper assembly 123, allowing for a firmer grasp, which implies that the system will also work reliably on large leaves.

A third set of experiments tested the ability of the present system to cut leaves. Four different types of leaves were tested: two small types and two large types. For both sizes, one type was flexible and thin, while the other was tougher. The large, tough leaves were also somewhat thicker, with a skeletal vein system. All three sets of blades were used in separate tests to cut the small leaves to ensure that all three work equally well. With the large leaves, all three blades had to work together to cut the sample.

All three sets of blades are able to consistently sever leaves completely. For the small leaves, every test resulted in either a complete sever or a partial sever. When the blades didn't cut completely through the leaf, one could still easily rip off the remaining part, meaning that aerial robotic platform 100 would successfully acquire and store the sample when it left the collection site.

For the big leaves, the present system also worked very well. The soft leaves were cut completely in almost every trial; again, in the trials with partial severing, the leaf easily tore free when gripper assembly 123 was pulled away. Overall, for target leaves, the system was successful in 87/90 trials. Only the set of tests using large, thick leaves showed decreased performance. In these trials, the blades did not cut completely through the leaf. For most of the trials, the leaf could still be easily removed even though the cut was not complete. The left, center, and right blades had a success rate of 3, 5, and 7 out of 10 trials respectively. However, these leaves do not simulate target leaves.

A final manual cutting test dealt with a more purposeful application—rose cutting. First, the same cutting tests were repeated on rose leaves. As expected, all three sets of blades had a 100% success rate, with ten trials per blade set. The system was subsequently tested on rose petioles, and the system again had a 100% success rate over ten trials with each set of blades.

A further test proceeded to measure the ability to cut stems. This test, unsurprisingly, showed a significant amount of variability because stems, even from the same plant, can vary in water content. For example, a stalk of a rose plant was held in the gripper assembly and cut using the front blades (presumably the ones cutting stems in flight). The results are summarized in Table 1 below:

TABLE 1

Ability of single blade to cut through rose stems

| Thickness (mm) | Success | Failure |
|---|---|---|
| 1 | 2 | 0 |
| 2 | 8 | 0 |
| 3 | 5 | 2 |
| 3.5 | 1 | 1 |
| 4 | 1 | 2 |

For 17 out of 22 trials, the system completely cut through the test stem or severed it enough for the experimenter to remove the sample easily with one hand. However, it should be noted that in another 5 trials, the blades could not reach the stem because of interference from leaves in the cutting interface. This test helps demonstrates feasibility because stems could occasionally enter the gripper system during sample collection, but the system would often be able to perform in those situations.

To perform many of these tests, a citrus tree was set up in an indoor lab space. The tree was about 2 meters tall. A pilot manually flew aerial robotic platform 100 so that the leaf entered into receptacle 121 of sample collector 120. The sample was then cut by the system, at which point aerial robotic platform 100 was landed, and the test could be repeated. The flights were conducted by the same pilot on two separate days.

After collecting data for citrus leaves, small, pointed leaves and large, thin leaves were attached to the tree using cable-ties. This test configuration was used to ensure that the system could grasp multiple types of leaves from a realistic plant structure.

Multiple approach angles were tested, and the sample acquisition success rate was quantified. First, it was observed that downwash did not interfere with sample collection, validating the design. In terms of multiple approach trajectories, candidate leaves hanging at a variety of angles were selected. Additionally, they were located on different branches spaced around the tree, so the pilot had to approach from different angles and heights while avoiding varying amounts of background foliage (i.e. other leaves that we weren't grasping). The success rate was quantified in two ways. The rate at which aerial robotic platform 100 successfully flew away with a plant sample when a leaf actually entered into sample collector 120 was examined; additionally, the rate at which the system was able to get a leaf into gripper assembly 123 was noted. For all flights, the frequency at the downwash prevented the system from collecting a sample was considered, but downwash from propellers 102 did not affect leaf acquisition in any of the test trials, demonstrating that the system was successfully designed for this interaction.

The results of the flight trials confirm the usability of aerial robotic platform 100 for phytobiopsy. With purely manual flight on citrus leaves, the test pilot was able to maneuver a leaf into the grasping mechanism in 16/21 (76%) of the trials. Of those 16 trials, 15/16 (94%) instances resulted in the leaf being removed. One outlier occurred because the sample grasped was a mature, thick leaf and the blades were dull after excessive use. Finally, 12/15 (80%) of the successful cuts resulted in the sample securely sitting in the collection mechanism. In the case where the leaf did not cut properly (trial 6), aerial robotic platform 100 crashed. However, the likelihood of this error can be minimized once an autonomy stack is implemented. Fail-safes can be implemented to force the system to release and attempt a new approach trajectory.

Upon the end of first collection day, significant plant matter build-up was observed on the blades, hence they were replaced with new units, and the cutting action was immediately observed to have improved. Specifically, the ability to cut the tough leaves that caused the crash was tested, and it was observed that the system could now sever those leaves. On day two, the system experienced no crashes and no instances of partial severing of a leaf.

With the small, pointed leaves and the large, thin leaves, the sample was cut successfully in 6/6 trials in which the leaf entered the system, with 4 of these trials being complete successes, 1 trial ending with the leaf trapped in the blade mechanism instead of the collection mechanism, and 1 trial ended with a successful collection, but the system could not be stabilized after the leaf suddenly cut (i.e. upon severing the leaf, the reaction forces changed suddenly, causing the crash). Had this system been fully autonomous, it likely would have recovered. Additionally, this unusual cut occurred on day 1 with the observed dull blades. Even though the system did crash, it demonstrated its physical robustness by sustaining minimal damage. There was also 1 small leaf trial in which the leaf did not enter the gripper.

Overall, the present phytobiopsy system's feasibility is demonstrated in a few ways. First, in 12/16 (75%) trials in which a sample entered the system, a leaf section was successfully removed and retained inside the collection mechanism. A significant source of variability in the system appears to be the pilot, implying that performance will only increase with autonomy. Second, the tests described above were completed with essentially the same success rate across two separate testing days (replacing the blades for day two actually improved the cutting reliability). Third, despite two crashes, the lightweight system sustained only minor damage to the arm. Fourth, the system was able to successfully collect samples from multiple types of leaves that varied in thickness and size. These leaves hung at different angles, heights, and locations relative to a citrus tree structure.

Accordingly, with the presently-disclosed systems, devices, and methods, the results demonstrate a 98.0% success rate for cutting target plant samples, a 93.8% success rate for severing a sample leaf during manual flight tests in which the sample entered the system, and an 80.0% success rate for securely storing the sample properly once severed during manual flight tests.

In another embodiment, the present subject matter provides an environmental sensor probe 130 that can be deployed and recovered autonomously (e.g., by a UAV or other aerial robotic platform 100). The basic probe design may be adapted to collect a variety of environmental samples that can be transported autonomously for offsite analysis. In some embodiments, such a probe 130 may be deployed to monitor and/or collect samples (e.g., passively) from the environment at or near a plant of interest, and probe 130 may then be collected at a later time to study the information and sample materials collected. In this regard, probe 130 according to this embodiment may be configured for persistent collection of air, soil, or pest samples over the course of an extended period (e.g., hours to days).

In some particular embodiments, for example, probe 130 may be designed as a pest trap (e.g., for pest density monitoring). For efficient spraying decisions in agriculture, it may be valuable to periodically collect and analyze pest samples. Currently, this collection is done manually by laying insect traps that have to be recovered manually for ex-situ analysis. Alternatively or in addition, probe 130 may be adapted for other applications such as taking fungal spore samples, collecting data on specific air pollutants, and/or monitoring prevalence of insects known to be vectors for agriculture, wildlife, and/or human diseases.

Regardless of the type of sample to be obtained, the present systems, devices, and methods may include a smart sensor probe 130 that can be deployed and recovered by an aerial robotic platform 100 (e.g., an autonomous UAV), and samples taken by probe 130 may thereby be brought in for off-site analysis. Probe 130 can be deployed in the field and recovered to provide information about the conditions surrounding the agricultural environment. For example, in some embodiments, the number of specific pests that are around the crops at different times of day may be monitored. Alternatively, in some embodiments, it may be beneficial to take fungal spore samples. Being able to collect physical samples of fungal spores for off site testing will help provide information regarding the conditions surrounding the plant of interest.

Regarding the particular design of probe 130, an embodiment is illustrated in FIG. 10. In this embodiment, probe 130 includes first coupling member 131 that is configured to couple with a complementary docking interface 117 on aerial robotic platform 100 as discussed below. In the particular configuration illustrated in FIG. 10, for example, first coupling member 131 comprises a top docking funnel 132 having a shape, size, and/or other configuration that is designed to optimize the ability of aerial robotic platform 100 to selectively engage probe 130. Specifically, for example, the substantially horn-shaped configuration of docking funnel 132 may be designed such that a complementary docking interface 117 of aerial robotic platform 100 is guided to a first engagement element 133 (e.g., a magnet or ferromagnetic disc) at or near a center of docking funnel 132. Specifically, for example, in some embodiments, the complementary docking interface 117 of aerial robotic platform 100 includes a second engagement element 118, such as a magnet (e.g., an electro-permanent magnet), that may be coupled to first engagement element 133 to couple probe 130 to aerial robotic platform 100. The geometry of first coupling member 131 ensures robustness against alignment errors during such mating. Although a particular configuration for probe 130 is disclosed above, any of a variety of other configurations for first coupling member 131 and docking interface 117 can be used for selectively coupling probe 130 to aerial robotic platform 100.

Referring still to the embodiment of probe 130 shown in FIG. 10, probe 130 may further include a narrow cylindrical midsection 134 or other structural element that is connected to first coupling member 131. Cylindrical midsection 134 can be of a desired length that helps to define the height of probe 130 depending on the application. For example, in the illustrated configuration, a 120 cm double-sided funnel sits on top of a 3 cm tall, 110 mm diameter empty cylinder. In some embodiments, first engagement element 133 (e.g., a ferromagnetic disc) may be held within cylindrical midsection 134 (e.g., in a cylindrical well) at or near the junction with first coupling member 131 (e.g., at an end of cylindrical midsection 134 adjacent to a base of docking funnel 132).

A sample collector 140 may further be defined in probe 130. In the embodiment shown in FIG. 10, for example, a sample collection space 141 is defined around narrow cylindrical midsection 134. In some embodiments, sticky tapes may be mounted inside probe 130 to trap insects or other samples within sample collection space 141. In addition, in some embodiments, a camera may be provided that takes periodic photos of the sticky tape to log the progression of insect trapping.

Figure 11A:
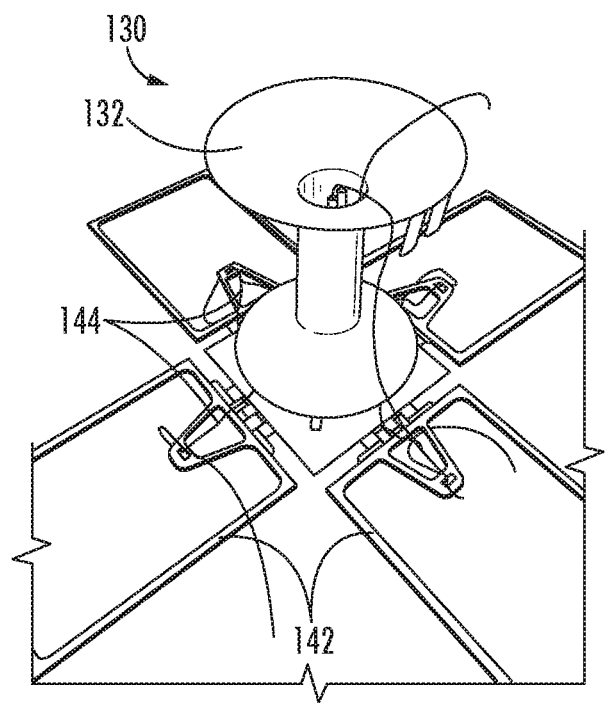
FIGS. 11A and 11B are perspective side view of an environmental probe in open and closed positions, respectively, according to an embodiment of the presently disclosed subject matter.
Figure 11B:
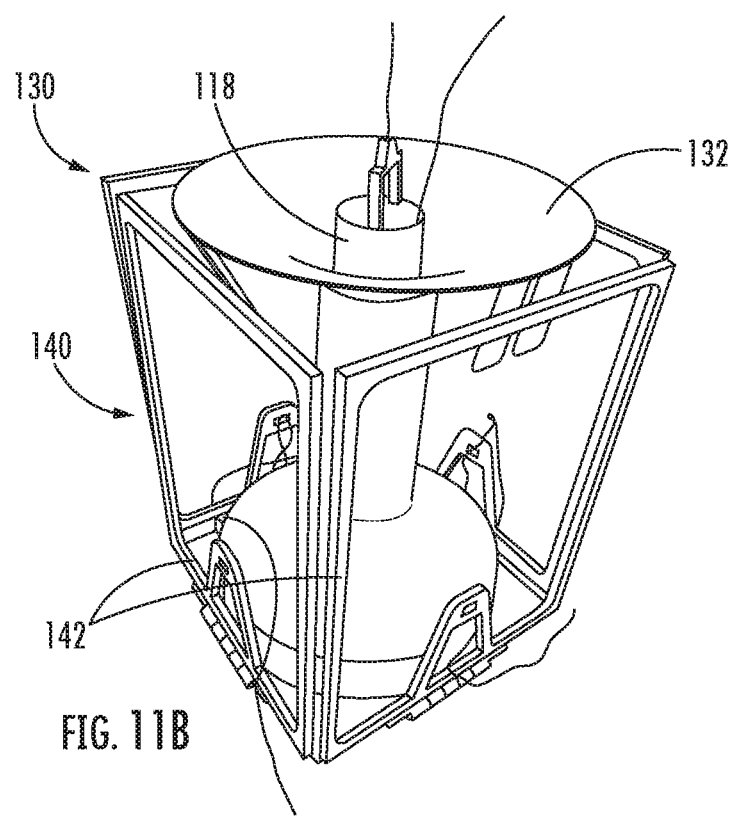
Figure 12:
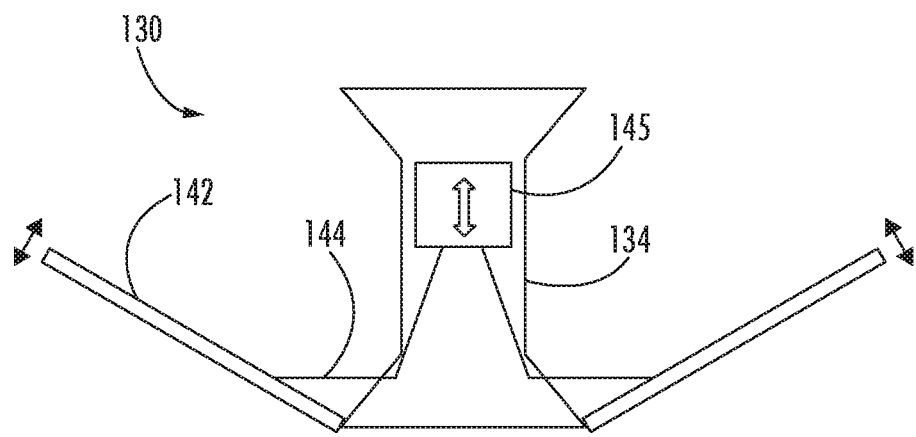
FIG. 12 is a side sectional view of elements of an environmental probe according to an embodiment of the presently disclosed subject matter.
Figure 13A:
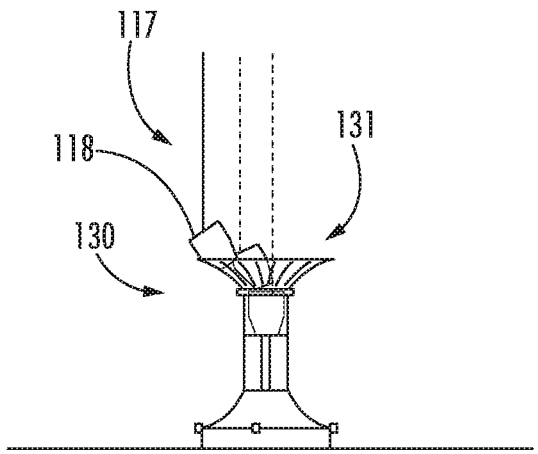
FIGS. 13A-D are side views of an environmental probe in various stages of engagement with a UAV according to embodiments of the presently disclosed subject matter.
Figure 13B:
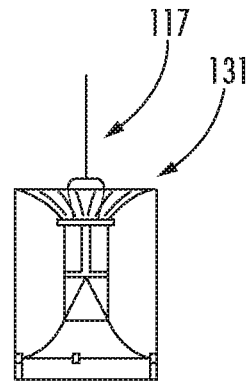
Figure 13C:
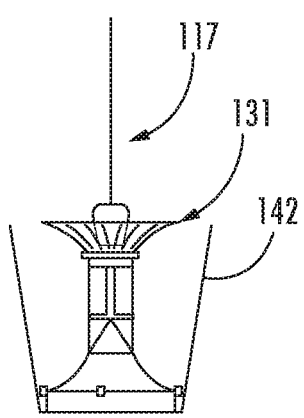
Figure 13D:
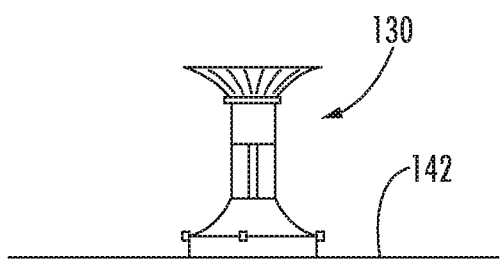

Probe 130 may be designed so that this space 141 is substantially enclosed during flight but is exposed when deployed. In this way, whatever field samples are taken will be protected in flight. In some embodiments, for example, one or more containment flaps 142 (e.g., four panels are used in the embodiment of FIG. 10) are attached to probe 130 (e.g., hingedly connected to the bottom of probe 130) and are movable to selectively pivot away from or towards cylindrical midsection 134. As illustrated in FIGS. 11A and 11B, for example, corresponding cables 144 may be attached to flaps 142, cables 144 being selectively movable to cause the pivoting of flaps 142.

In some embodiments, cables 144 are connected to the bottom of a movable component 145 (e.g., a piston) positioned within cylindrical midsection 134, and this movable component 145 may be connected to first engagement element 133 (e.g., a ferromagnetic disc). In this configuration, cables 144 may go down the length of the inside of cylindrical midsection 134 and leave the system through holes in the top of a bottom portion of cylindrical midsection 134 (See, e.g., FIGS. 12 and 13A-13D). Cables 144 may then be attached to flaps 142 (e.g., about 10 cm from the bottom of each of flaps 142).

In this arrangement, when first engagement element 133 is engaged by the corresponding second engagement element 118 of docking interface 117 of aerial robotic platform 100 (See, e.g., FIG. 13A), movable component 145 is pulled upward by the connection to second engagement element 118. This upward movement of movable component 145 pulls up cables 144 to cause flaps 142 to close around cylindrical midsection 134 to isolate sample collector 140 from the external environment (See, e.g., FIG. 13B). Conversely, when first engagement element 133 is decoupled from second engagement element 118 (e.g., when probe 130 is deployed in the environment to be studied), movable component 145 may move downwardly into cylindrical midsection 134, relieving tension on cables 144 such that flaps 142 may pivot outwardly (See, e.g., FIG. 13C), thus opening sample collector 140 and exposing sample collection space 141 to the external environment. (See, e.g., FIG. 13D)

In addition, in some embodiments, probe 130 may include small, light weight solar panels. With such a feature, the system may be able to power itself for extended periods of time, which may beneficially allow probe 130 to perform tasks such as pumping $CO_2$ to attract certain insects. The inclusion of solar panels may also allow probe 130 to be used as a charging station for aerial robotic platform 100 in the field. This may make aerial robotic platform 100 more efficient as it would have the ability to stay out in the field longer and would not have to come back in to be charged each time it starts to run out of battery.

In some embodiments, all of the components of probe 130 may be made of 3D printed material except flaps 142, which may be laser cut out of medium density fiberboard. In particular, docking funnel 132 may be composed of ABS-M30 (white) having a layer thickness of 0.005 inches and a shell thickness of 2.8 mm. A honeycomb fill may be used for its high stress resistance and low weight/density. This configuration allows probe 130 to endure multiple drops from aerial robotic platform 100 without losing structural integrity. That being said, those having ordinary skill in the art will recognize that any of a variety of other material compositions and/or configurations may be used to balance the desire for increased robustness to field conditions, while at the same time improving the ease of docking and also reducing the probe's aerodynamic footprint, as it is in the direct downwash of the propellers of aerial robotic platform 100.

As discussed above, to deploy and collect the environmental probe, aerial robotic platform 100 may be equipped with a docking interface 117 that is configured to selectively engage and transport probe 130. Referring to one embodiment shown in FIG. 14, docking interface 117 in which second engagement element 118 is movable relative to aerial robotic platform 100 (e.g., second engagement element 118 is cable-suspended from aerial robotic platform 100) may be used. In some embodiments, second engagement element 118 is a system consisting of an electro-permanent magnet (e.g., 12V) in a cylindrical housing that is hung on a string connected to aerial robotic platform 100 to allow mating with first engagement element 133 (e.g., a ferromagnetic disc) centered on docking funnel 132 of probe 130 as described above. It should be understood by those having ordinary skill in the art, however, that any of a variety of other connection structure may be used to allow second engagement element 118 to be moved into a desired position for operation of docking interface 117.

Regardless of the particular configuration by which second engagement element 118 is connected to aerial robotic platform 100, to deploy probe 130, the electro-permanent magnet is briefly activated (e.g., with a DC current), releasing probe 130. Alternatively, an electromagnet may be used in place of the electro-permanent magnet, although use of an electro-permanent magnet ensures that power is not wasted during transit. In this regard, the electro-permanent magnet may be 'energized' by default, which saves battery life by not using an electric current to constantly create a magnetic field to hold probe 130. The magnetic coupling may then be 'released' by briefly passing an electric current through the built-in coil, at least substantially negating the permanent magnet's field and releasing the payload.

Regardless of the particular docking system used to selectively couple probe 130 to aerial robotic platform 100, aerial robotic platform 100 may be designed, configured, and/or controlled to efficiently locate and collect environmental probe 130 from its monitoring location. In this regard, any of a several probe detection algorithms may be used to accurately detect probe 130. In some embodiments, for example, a method of detecting probe 130 may include identifying the substantially circular shape of top funnel 132 (e.g., using OpenCV's Hough Circle Transform function).

Figure 15:
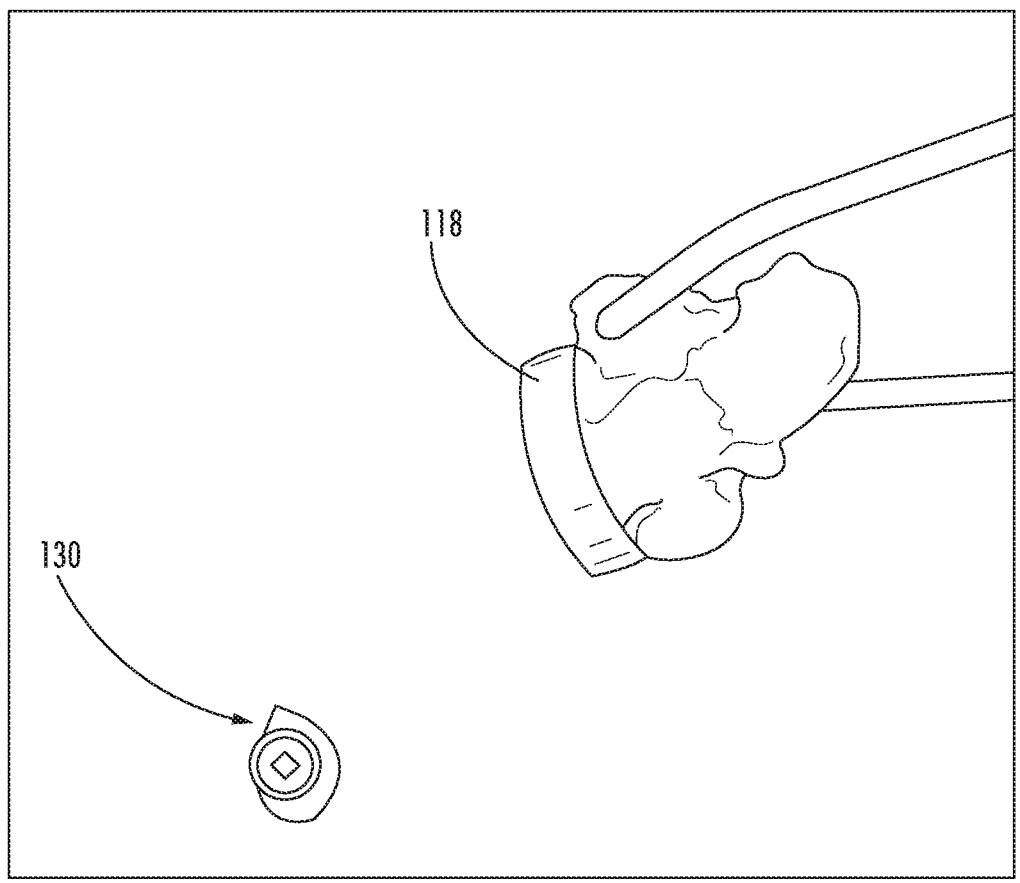
FIG. 15 is a visualization of the UAV detecting the probe using the downward-facing camera while in-flight.

This identification may involve a visual identification using a downward-facing camera, laser scanning system, and/or sonar sensor. Alternatively or in addition, a method of detecting probe 130 may include detecting the color and shape of concentric rings provided in funnel 132 of probe 130. (See, e.g., FIG. 15)

In either configuration, aerial robotic platform 100 may be configured to detect ellipses instead of circles because the probe will likely appear as an ellipse whenever aerial robotic platform 100 is not directly above it. First, the algorithm may identify when the colors of interest exceed a predetermined threshold in the image and find all contiguous regions. For each region, the eccentricity, size, and rotation may be calculated (e.g., using OpenCV), and an equivalent ellipse may be generated. The ellipse may then superimposed onto the original region, and the error may be calculated by the sum of the squares of the differences between the bounding points of the two shapes. This process can produce a value for how 'ellipse-like' each region is. Throwing out all of the shapes that were not ellipses, the program may check for concentric regions. If it found that the centers of two regions are close relative to their sizes, the method may output their centroid. This algorithm has been shown to work well indoors. Since the present subject matter is particularly applicable in large outdoor environments, however, the parameters of the detection method may be tuned to maximize performance in outdoor conditions. In this regard, the identification may be configured to compensate for sun, shadows, wind, and/or any of a variety of environmental conditions. For example, calibration of the color and white balance of the downward facing camera in bright sunlight may improve the ability of the system to identify probe 130.

Aerial robotic platform 100 flies to the expected position of probe 130 for pickup. Once above this initial waypoint, generally designated 150, it searches for probe 130 in the nearby area until it detects probe 130 using the downward-facing camera. In some embodiments, the search pattern used is an expanding square search pattern (e.g., with approximately 1 meter spacing). This search pattern was used for its simplicity to implement, as each waypoint can be generated using the following simple equation.

$$y(n) = \left[\frac{n}{4}\right](-1)^{\left[\frac{n-1}{2}\right]}$$
$$x(n) = y(n-1)$$

Figure 16:
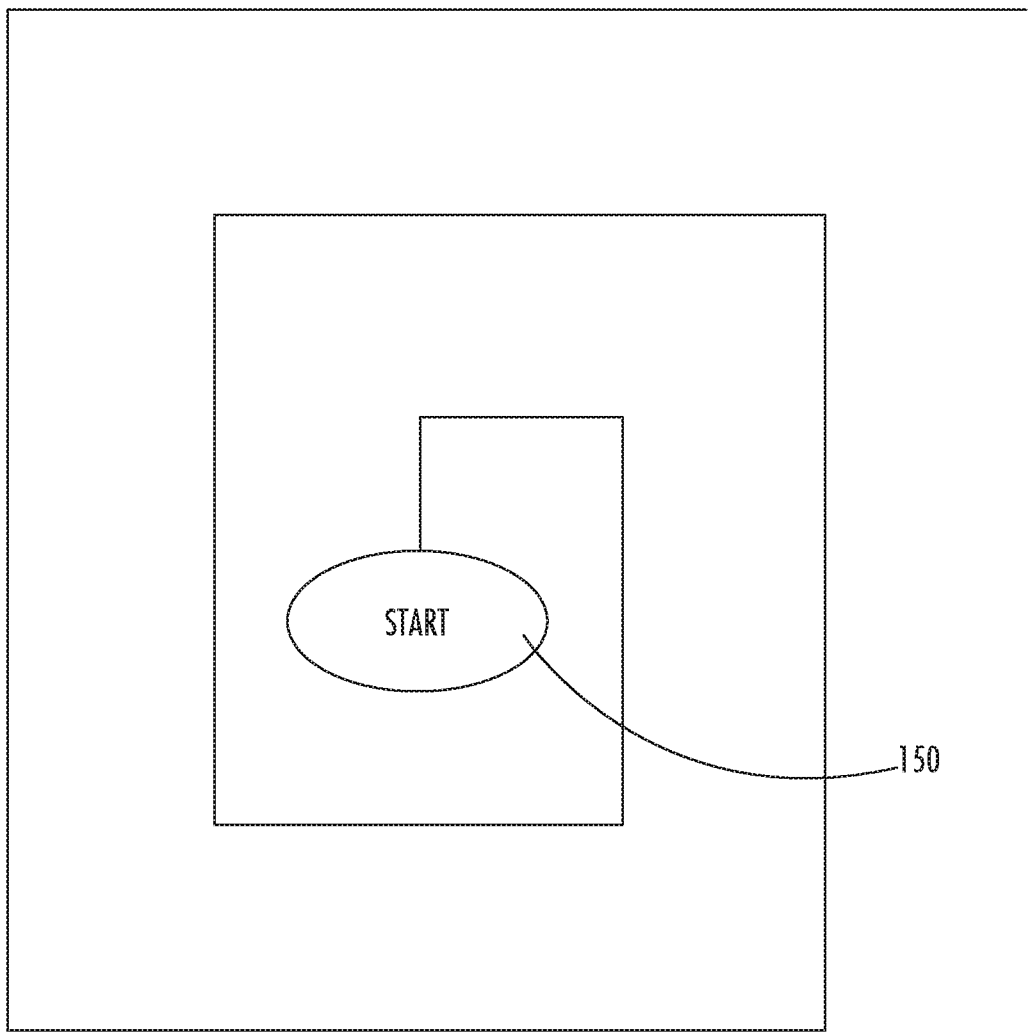
FIG. 16 is a diagram of a search pattern used to locate an environmental probe at an expected position according to an embodiment of the presently disclosed subject matter.

The visualization of this search pattern can be seen in FIG. 16. Once the probe detection algorithm detects probe 130 using the downward-facing camera, aerial robotic platform 100 centers itself directly above probe 130. Aerial robotic platform 100 then lowers itself onto probe 130, with second engagement element 118 (e.g., the electromagnet) making contact with first engagement element 133 (e.g., the ferromagnetic disc) on probe 130. Once this contact is established, the payload is attached, and aerial robotic platform 100 can continue its mission.

In addition, in some embodiments, should aerial robotic platform 100 fail to engage probe 130 on a given collection attempt, aerial robotic platform 100 may be configured to automatically reattempt to detect and make contact with probe 130. In some embodiments, such reattempt may involve moving aerial robotic platform 100 to a predetermined distance above probe 130 and reorienting the position of aerial robotic platform 100 with respect to probe 130 before lowering itself again towards probe 130 such that second engagement element 118 may make contact with first engagement element 133 on probe 130. Such a process may be repeated until probe 130 is successfully engaged by aerial robotic platform 100.

In some embodiments, a string 136 may be connected between first engagement element 133 and docking funnel 132 in an effort to create a better connection between second engagement element 118 and the attachment point. With string 136 coiled underneath first engagement element 133, first engagement element 133 may be free to move as second engagement element 118 approaches. This freedom may allow an optimal connection to be established even if second engagement element 118 is not perfectly aligned with first engagement element 133 on a collection attempt.

Figure 14:
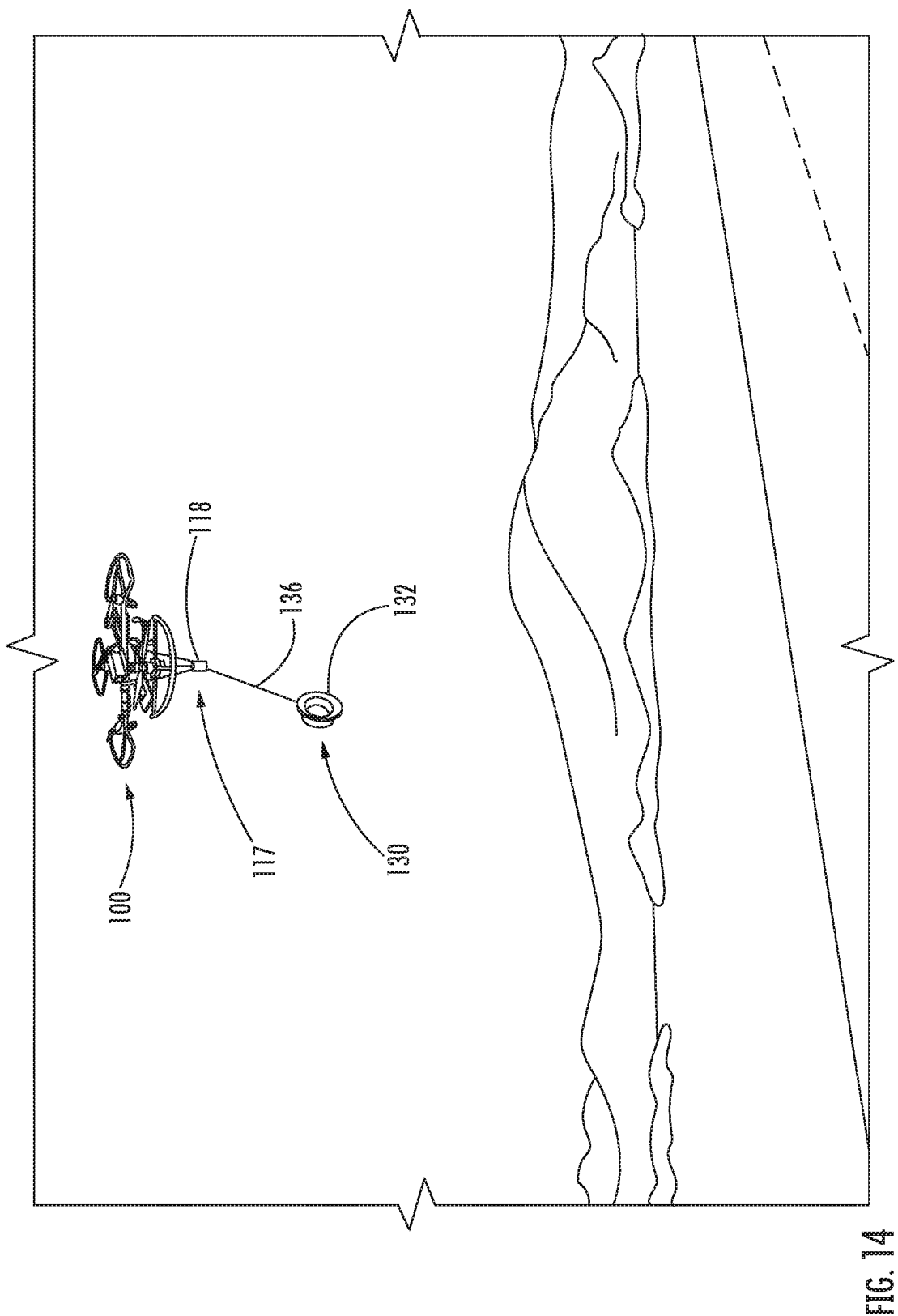
FIG. 14 is a perspective side view of a UAV retrieving an environmental probe according to an embodiment of the presently disclosed subject matter.

Once aerial robotic platform 100 picks up probe 130, it flies to the deployment waypoint by switching from an off-board mode back to a mission mode. The mission controller constantly monitors a distance from aerial robotic platform 100 to the deployment waypoint. As aerial robotic platform 100 approaches this waypoint, it descends to a predetermined low altitude (e.g., approximately 1 meter above the ground). Once the distance from the deployment waypoint is below a set amount (e.g., 2 meters), the mission controller may deactivate second engagement element 118 and release the payload. As discussed above, this release may be done by briefly turning on a current to the coil in an electro-permanent magnet that is selected to at least substantially cancel out the permanent magnetic field. In some embodiments in which probe 130 is coupled to aerial robotic platform 100 by string 136, probe 130 may fall upright more often. Because probe 130 may be designed to be automatically released when aerial robotic platform 100 descends to a selected height (e.g., at 2 meters), it often flipped upside-down, but the additional length provided by string 136 may reduce the fall distance as seen in FIG. 14.

In some embodiments, a mission manager executes each of the above algorithms and keeps track of the progress of aerial robotic platform 100 within the mission. It also automatically switches between different operating modes, such as mission and off-board modes according to the specific task that needs to be completed. In order to simplify the controller for aerial robotic platform 100, a stand-alone object-oriented library was written to send commands to aerial robotic platform 100. The locations at which to execute particular tasks were given as waypoints to the flight controller and waypoint indices to the top-level mission controller. For executing a simple mission, for example, aerial robotic platform 100 may take-off to a first waypoint, pick up probe 130 at a second waypoint, deploy probe 130 at a third waypoint, and land at a fourth waypoint. The waypoint indices at which of these actions occurs may be rearranged, thus allowing more complex paths to be taken, such as multiple waypoints between pickup and deployment to avoid a no-fly zone.

To enable this deployment and collection of probe 130 with aerial robotic platform 100, in some embodiments, the cost of such as system may be under $3000, and the total takeoff weight is 2.3 Kg. Compared to the on-board sample collection embodiment discussed above, the differences in cost and weight may at least in part be attributed to additional sensing and computing components (e.g., onboard computing, cameras, and high gain communication link) that are used to efficiently locate and collect the environmental probe from its monitoring location as discussed above.

Experimental Evaluation

The present systems, devices, and methods were tested indoors in the flight-testing lab at the University of Pennsylvania. This lab features over 20 motion-capture VICON cameras that calculate the position of aerial robotic platform 100 in real-time and stream it to the onboard computer over Wi-Fi. Aerial robotic platform 100 integrates this position data into a local position estimator, providing extremely accurate 3D pose. Since the MOCAP system provides accuracy much higher than conditions encountered outdoors with GPS noise in meters, the probe pickup algorithm was tested without MOCAP data integration. Positional information was instead calculated using the internal IMU and Optical camera.

Once the software was successfully tested indoors, the present systems, devices, and methods were further studied in an outdoor flight-testing setup. At this stage, larger missions were flown and the focus shifted to calibration, and tuning of the probe detection algorithm. Field trials were conducted at the NSF sponsored student UAV competition, where the goal was to develop a UAV to deploy and recover a scale-model of the Microsoft Research Premonition Project's mosquito trap assembly. Accordingly, a modified version of the original probe design was used to meet the needs of this trial, although it is believed that the results of this field testing remain applicable to any of a variety of probe designs, including the particular configurations discussed above. The field trials were able to successfully demonstrate fully autonomous takeoff, mission navigation, probe deployment, and landing.

The present subject matter can be embodied in other forms without departure from the spirit and essential characteristics thereof. The embodiments described therefore are to be considered in all respects as illustrative and not restrictive. For example, the systems, devices, and methods discussed above utilize a UAV platform, but those having ordinary skill in the art will recognize that the principles discussed herein can be readily applied to other transport modalities, such as on a ground robot for use in heterogeneous co-robot teams (e.g., UAVs or ground robots depending on farm setting), allowing for efficient disease detection and enabling improved food production. Furthermore, the precision payload pickup and deployment capabilities have applications outside agricultural work, including but not limited to UAV package delivery or other precision aerial manipulation tasks. Accordingly, although the present subject matter has been described in terms of certain preferred embodiments, other embodiments that are apparent to those of ordinary skill in the art are also within the scope of the present subject matter.

The disclosure of each of the following references is incorporated herein by reference in its entirety.

REFERENCES

[1] S. Sarkar, J. Das, R. Ehsani, and V. Kumar, "Towards autonomous phytopathology: Outcomes and challenges of citrus greening disease detection through close-range remote sensing," in IEEE International Conference on Robotics and Automation. IEEE, 2016, pp. 5143-5148.

[2] J. Thomas, J. Polin, K. Sreenath, and V. Kumar, "Avian-Inspired Grasping for Quadrotor Micro UAVs," in IDETC/CIE. ASME, 2013.

[3] M. Luo, W. Lu, B.-Y. Sun, and T. Mei, "Autonomous grasping of a space robot multisensory gripper," in IROS, 2006.

[4] J. Thomas, G. Loianno, K. Daniilidis, and V. Kumar, "Visual servoing of quadrotors for perching by hanging from cylindrical objects," Robotics and Automation Letters, IEEE, vol. PP, no. 99, pp. 1-1, 2015.

[5] "Towards Model-predictive Control for Aerial Pick-and-place," in IEEE International Conference on Robotics and Automation (ICRA), 2015.

[6] F. Huber, K. Kondak, K. Krieger, D. Sommer, M. Schwarzbach, M. Laiacker, I. Kossyk, S. Parusel, S. Haddadin, and A. Albu-Sch"affer, "First analysis and experiments in aerial manipulation using fully actuated redundant robot arm." in IEEE/RSJ International Conference on Intelligent Robots and Systems. IEEE, 2013, pp. 3452-3457.

[7] "Co-Robotic Device for Automated Tuning of Emitters to Enable Precision Irrigation," in IEEE International Conference on Automation Science and Engineering, (CASE), 2016.

[8] T. L. Koushil Sreenath and V. Kumar, "Geometric Control and Differential Flatness of a Quadrotor UAV with a Cable suspended Load," in IEEE Conference on Decision and Control, 2013.

[9] "A Multilayer Control for Multirotor UAVs Equipped with a Servo Robot Arm," in IEEE International Conference on Robotics and Automation (ICRA), 2015.

[10] "Modeling the Forces of Cutting With Scissors," in IEEE Transactions on Biomedical Engineering, vol. 55, no. 3, 2008, pp. 848-56.

[11] L. Meier, D. Honegger, and M. Pollefeys, "PX4: A node based multithreaded open source robotics framework for deeply embedded platforms," in Robotics and Automation (ICRA), 2015 IEEE International Conference on, may 2015.

[12] J. Das, G. Cross, C. Qu, A. Makineni, P. Tokekar, Y. Mulgaonkar, and V. Kumar, "Devices, systems, and methods for automated monitoring enabling precision agriculture," in 2015 IEEE International Conference on Automation Science and Engineering (CASE), August 2015, pp. 462-469.

[13] S. Sarkar, J. Das, R. Ehsani, and V. Kumar, "Towards autonomous phytopathology: Outcomes and challenges of citrus greening disease detection through close-range remote sensing," in IEEE International Conference on Robotics and Automation. IEEE, 2016, pp. 5143-5148.

[14] J.-P. Ore, S. Elbaum, A. Burgin, and C. Detweiler, "Autonomous aerial water sampling," Journal of Field Robotics, vol. 32, no. 8, pp. 1095-1113, 2015. [Online]. Available: http://dx.doi.org/10.1002/rob.21591

[15] D. G. Schmale Iii, B. R. Dingus, and C. Reinholtz, "Development and application of an autonomous unmanned aerial vehicle for precise aerobiological sampling above agricultural fields," Journal of Field Robotics, vol. 25, no. 3, pp. 133-147, 2008.

[16] "Microsoft Research Project Premonition," https://www.microsoft.com/en-us/research/project/project-premonition/, accessed: 2017 Feb. 26.

[17] L. Meier, D. Honegger, and M. Pollefeys, "PX4: A node-based multithreaded open source robotics framework for deeply embedded platforms," in Robotics and Automation (ICRA), 2015 IEEE International Conference on, may 2015.

[18] M. Quigley, K. Conley, B. Gerkey, J. Faust, T. Foote, J. Leibs, R. Wheeler, and A. Y. Ng, "ROS: an open-source Robot Operating System," in ICRA workshop on open source software, vol. 3, no. 3.2, 2009, p. 5.

[19] "MAVROS—MAVLink extendable communication node for ROS with proxy for Ground Control Station." http://wiki.ros.org/mavros, accessed: 2017 Feb. 26.

What is claimed is:

1. An agricultural sample collection system comprising:
an aerial robotic platform;
an arm assembly coupled to the aerial robotic platform and comprising an arm that extends away from the aerial robotic platform; and
a sample collector connected to a distal end of the arm, wherein the sample collector comprises:
a gripper assembly configured to grasp one or more samples of agricultural material on a plant to be analyzed;
a cutting assembly configured to selectively remove the one or more samples of agricultural material from the plant to be analyzed; and
a receptacle configured to receive the one or more samples of agricultural material therein.

2. The agricultural sample collection system of claim 1, wherein the arm assembly comprises a base coupled to the aerial robotic platform; and
wherein the arm is connected to the base but is movable with respect to the base to change a distance by which the arm extends away from the aerial robotic platform.

3. The agricultural sample collection system of claim 2, wherein the arm is pivotably coupled to the base.

4. The agricultural sample collection system of claim 2, wherein the arm is movable to a storage position in which the sample collector is positioned beneath the aerial robotic platform.

5. The agricultural sample collection system of claim 1, wherein the gripper assembly comprises:
a gripper tongue that is movable with respect to the receptacle to clamp the one or more samples of agricultural material on the plant to be analyzed between the gripper tongue and an upper peripheral edge of the receptacle.

6. The agricultural sample collection system of claim 1, wherein the cutting assembly comprises:
a first cutter arm that is movable with respect to the gripper assembly, wherein the first cutter arm includes one or more first blades; and
a second cutter arm that is movable with respect to the gripper assembly independently from the first cutter arm, wherein the second cutter arm includes one or more second blades.

7. A method for acquiring agricultural samples, the method comprising:
positioning an aerial robotic platform in proximity to a plant to be analyzed;
grasping one or more samples of agricultural material on a portion of the plant to be analyzed;
selectively removing the one or more samples of agricultural material from the plant to be analyzed; and
transporting the one or more samples to a remote location for ex-situ analysis of the one or more samples;
wherein grasping one or more samples of agricultural material on a portion of the plant to be analyzed comprises:
extending an arm assembly away from the aerial robotic platform; and
grasping the one or more samples of agricultural material on the portion of the plant to be analyzed with a sample collector connected to a distal end of the arm;
wherein selectively removing the one or more samples of agricultural material comprises severing the one or more samples of agricultural material from the plant to be analyzed with a cutting assembly provided on the sample collector; and
wherein transporting the one or more samples comprises storing the one or more samples in a receptacle formed in the sample collector.

8. The method of claim 7, wherein severing the one or more samples of agricultural material from the plant to be analyzed comprises:
actuating a first cutter arm that is movable with respect to the gripper assembly, wherein the first cutter arm includes one or more first blades; and
actuating a second cutter arm that is movable with respect to the gripper assembly independently from the first cutter arm, wherein the second cutter arm includes one or more second blades.

9. The method of claim 7, wherein transporting the one or more samples comprises retracting the arm assembly to a storage position in which the sample collector is positioned beneath the aerial robotic platform.

10. An agricultural sample collection system comprising:
an environmental sensor probe comprising a first coupling member including a first engagement element; and
an aerial robotic platform comprising a second coupling member including a second engagement element configured to be selectively coupled to the first engagement element;
wherein the environmental sensor probe comprises a sample collector, wherein the sample collector is configured to receive one or more environmental samples therein to be analyzed;
wherein the sample collector comprises a receptacle configured to receive the one or more environmental samples therein;
wherein the sample collector comprises one or more containment flaps that are movable between an open position in which the receptacle is exposed to an external environment and a closed position in which the one or more containment flaps close around the receptacle to at least substantially isolate the receptacle from the external environment;
wherein the one or more containment flaps are moved to the open position upon decoupling of the first engagement element from the second engagement element; and
wherein the one or more containment flaps are moved to the closed position upon coupling of the first engagement element from the second engagement element.

11. The agricultural sample collection system of claim 10, wherein the environmental sensor probe comprises a pest trap.

12. The agricultural sample collection system of claim 10, wherein the first coupling member comprises a docking funnel configured to guide the second coupling member into engagement with the first coupling member.

13. The agricultural sample collection system of claim 10, wherein the first engagement element comprises a ferromagnetic disc; and
wherein the second engagement element comprises a magnetic element.

14. The agricultural sample collection system of claim 13, wherein the magnetic element comprises an electro-permanent magnet.

15. A method for acquiring agricultural samples, the method comprising:
- positioning an environmental sensor probe in an area in proximity to a plant to be analyzed;
- collecting one or more environmental samples from the area in proximity to the plant to be analyzed, wherein collecting one or more environmental samples comprises exposing a receptacle on the environmental sensor probe to an environment in the area in proximity to the plant to be analyzed, and wherein exposing the receptacle on the environmental sensor probe to the environment comprises moving one or more containment flaps between a closed position in which the receptacle is at least substantially isolated from the environment and an open position in which the receptacle is exposed to the environment;
- coupling the environmental sensor probe to an aerial robotic platform;
- moving the one or more containment flaps to the closed position upon coupling the environmental sensor probe to the aerial robotic platform; and
- transporting the one or more environmental samples to a remote location for ex-situ analysis of the one or more environmental samples.

16. The method of claim 15, wherein positioning the environmental sensor probe in the area in proximity to the plant to be analyzed comprises:
- coupling the environmental sensor probe to the aerial robotic platform;
- moving the aerial robotic platform to the area in proximity to the plant to be analyzed; and
- decoupling the environmental sensor probe from the aerial robotic platform.

17. The method of claim 15, wherein collecting one or more environmental samples comprises collecting one or more pests in a sample collector of the environmental sensor probe.

18. The method of claim 15, wherein coupling the environmental sensor probe to an aerial robotic platform comprises;
- guiding a second coupling member on the aerial robotic platform into engagement with a first coupling member on the environmental sensor probe; and
- coupling a first engagement element of the first coupling member to a second engagement element of the second coupling member.

* * * * *